(12) United States Patent
Van Heteren et al.

(10) Patent No.: US 11,896,851 B2
(45) Date of Patent: *Feb. 13, 2024

(54) RADIATION THERAPY SYSTEM USING A DIGITAL TOMOSYNTHESIS PROCESS FOR NEAR REAL-TIME LOCALIZATION

(71) Applicant: Varian Medical Systems, Inc., Palo Alto, CA (US)

(72) Inventors: John Van Heteren, Foster City, CA (US); Liangjia Zhu, Menlo Park, CA (US); Daniel Morf, Buch am irchel (CH)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 175 days.

This patent is subject to a terminal disclaimer.

(21) Appl. No.: 17/467,270

(22) Filed: Sep. 5, 2021

(65) Prior Publication Data
US 2021/0393989 A1      Dec. 23, 2021

Related U.S. Application Data

(63) Continuation of application No. 16/452,498, filed on Jun. 25, 2019, now Pat. No. 11,110,300.
(Continued)

(51) Int. Cl.
*A61N 5/10*      (2006.01)
*A61B 6/03*      (2006.01)
(Continued)

(52) U.S. Cl.
CPC ......... *A61N 5/1081* (2013.01); *A61N 5/1067* (2013.01); *A61B 6/032* (2013.01);
(Continued)

(58) Field of Classification Search
CPC .. A61N 5/1067; A61N 5/1081; A61N 5/1038; A61N 5/1039; A61N 5/107;
(Continued)

(56) References Cited

U.S. PATENT DOCUMENTS

| 6,535,574 B1 | 3/2003 | Collins et al. |
| 7,778,691 B2 | 8/2010 | Zhang et al. |

(Continued)

FOREIGN PATENT DOCUMENTS

| CN | 101422372 A | 5/2009 |
| CN | 101623198 A | 1/2010 |

(Continued)

OTHER PUBLICATIONS

International Search Report and Written Opinion of the International Searching Authority, International application No. PCT/US2019/043827, dated Oct. 17, 2019.
(Continued)

*Primary Examiner* — Irakli Kiknadze
(74) *Attorney, Agent, or Firm* — SU IP CONSULTING

(57) ABSTRACT

A method of radiation therapy comprises, while a gantry of a radiation therapy system rotates continuously in a first direction through a treatment arc from a first treatment delivery position to a second treatment delivery position, causing an imaging X-ray source mounted on the gantry to direct X-rays through a target volume and receiving a set of X-ray projection images from an X-ray imager mounted on the gantry; determining a current location of the target volume based on the set of X-ray projection images; and while the gantry to continues to rotate to the second treatment delivery position, initiating delivery of a treatment beam of a treatment-delivering X-ray source mounted on the gantry to the target volume, and continuing to cause the gantry to rotate in the first direction from the second (Continued)

treatment delivery position to a third treatment delivery position.

20 Claims, 16 Drawing Sheets

Related U.S. Application Data

(60) Provisional application No. 62/711,483, filed on Jul. 28, 2018.

(51) Int. Cl.
*G06T 7/00* (2017.01)
*G06T 11/00* (2006.01)
*A61B 6/00* (2006.01)

(52) U.S. Cl.
CPC .............. *A61B 6/541* (2013.01); *A61N 5/107* (2013.01); *A61N 5/1031* (2013.01); *A61N 5/1038* (2013.01); *A61N 5/1039* (2013.01); *A61N 5/1049* (2013.01); *A61N 5/1071* (2013.01); *A61N 2005/1054* (2013.01); *A61N 2005/1061* (2013.01); *G06T 7/0012* (2013.01); *G06T 11/008* (2013.01); *G06T 2207/10081* (2013.01); *G06T 2207/20081* (2013.01)

(58) Field of Classification Search
CPC .... A61N 2005/1061; A61N 2005/1074; A61N 5/1049; A61N 5/1031; A61N 2005/1054; A61N 5/1071; A61N 5/1045; A61N 5/1075; A61N 5/1068; A61N 5/1043; A61N 5/103; A61N 5/1083; A61N 5/1037; A61N 5/1036; A61N 2005/1052; A61N 2005/1055; A61N 2005/1091; A61N 5/1048; A61N 5/1064; A61N 5/1065; A61N 5/1042; A61N 5/1069; A61N 2005/1051; A61N 2005/1059; A61N 5/10; A61N 2005/1072; A61N 2005/1058; A61B 6/032; A61B 6/541; A61B 6/4085; A61B 6/03; A61B 6/4007; A61B 6/56; A61B 6/566; A61B 6/06; A61B 6/037; A61B 6/563; A61B 6/405; A61B 6/4092; A61B 6/4417; A61B 6/4014; A61B 6/5288; A61B 6/4447; A61B 6/4452; A61B 6/48; A61B 2090/3966; A61B 5/1121; A61B 5/1135; A61B 90/39; A61B 2090/376; A61B 2090/363; A61B 5/113; A61B 2090/3937; G06T 7/0012; G06T 11/008; G06T 2207/10081; G06T 2207/20081
USPC .................................................. 378/4, 19, 65
See application file for complete search history.

(56) References Cited

U.S. PATENT DOCUMENTS

| | | | |
|---|---|---|---|
| 8,002,465 | B2 | 8/2011 | Ahn |
| 8,660,325 | B2 | 2/2014 | Kaus et al. |
| 9,844,684 | B2 | 12/2017 | Luan et al. |
| 10,182,772 | B1 | 1/2019 | Rotman et al. |
| 11,027,153 | B2 | 6/2021 | Van Heteren et al. |
| 11,110,300 | B2 * | 9/2021 | Van Heteren ........ A61N 5/1067 |
| 2009/0283682 | A1 | 11/2009 | Star-Lack et al. |
| 2010/0183118 | A1 | 7/2010 | Star-Lack et al. |
| 2011/0080990 | A1 | 4/2011 | Filiberti et al. |
| 2012/0014501 | A1 | 1/2012 | Pele et al. |
| 2012/0230464 | A1 | 9/2012 | Ling et al. |
| 2013/0188856 | A1 | 7/2013 | Adler, Jr. et al. |
| 2015/0126796 | A1 | 5/2015 | Yan et al. |
| 2016/0184608 | A1 | 6/2016 | Adler, Jr. et al. |
| 2016/0310086 | A1 | 10/2016 | Besson |
| 2017/0108453 | A1 | 4/2017 | Foland et al. |
| 2018/0056090 | A1 | 3/2018 | Jordan et al. |
| 2019/0134425 | A1 * | 5/2019 | van Baar ............. A61N 5/1077 |
| 2019/0156497 | A1 * | 5/2019 | Berlinger ................ G06T 7/251 |
| 2019/0240508 | A1 * | 8/2019 | Friman ................. G06F 3/0346 |
| 2020/0030633 | A1 | 1/2020 | Van Heteren et al. |

FOREIGN PATENT DOCUMENTS

| | | |
|---|---|---|
| CN | 102341044 A | 2/2012 |
| CN | 103229178 A | 7/2013 |
| CN | 104884126 A | 9/2015 |
| CN | 106572835 A | 4/2017 |
| DE | 102011075341 A1 | 11/2012 |
| DE | 102011081422 A1 | 2/2013 |
| JP | 2000139892 A | 5/2000 |
| WO | 2011156526 A2 | 12/2011 |
| WO | 2017180513 A1 | 10/2017 |

OTHER PUBLICATIONS

International Search Report and Written Opinion of the International Searching Authority, International application No. PCT/US2019/043826, dated Oct. 17, 2019.
International Preliminary Report on Patentability, International application No. PCT/US2019/043826, dated Feb. 2, 2021.

* cited by examiner

RADIATION THERAPY SYSTEM USING A DIGITAL TOMOSYNTHESIS PROCESS FOR NEAR REAL-TIME LOCALIZATION

CROSS-REFERENCE TO RELATED APPLICATIONS

The present application is a continuation under 35 U.S.C. § 120 of U.S. patent application Ser. No. 16,452,498, filed Jun. 25, 2019, which claims the benefit of U.S. Provisional Application No. 62/711,483, filed Jul. 28, 2018. The present application is also related in subject matter to U.S. patent application Ser. No. 16/452,505. The aforementioned U.S. Provisional Application and U.S. patent applications, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three dimensional image of the target tissue and surrounding area. From such imaging, the size and mass of the target tissue can be estimated and an appropriate treatment plan generated and planning target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a radiation therapy system is configured to enable imaging and treatment of a target volume during a single patient breath hold. Specifically, in the embodiments, the radiation system includes a rotating gantry on which are mounted a treatment-delivering X-ray source and multiple imaging X-ray sources and corresponding X-ray imaging devices. The multiple imaging X-ray sources and X-ray imaging devices enable the acquisition of volumetric image data for the target volume over a relatively short rotational arc, for example 30 degrees or less. As a result, intra-fraction motion (anatomical variations occurring during a single patient breath-hold, for example due to peristalsis, gas bubble motion, loss of breath hold, and the like) can be detected in near-real time, for example within about one second or less. Thus, the radiation therapy system can perform image guided radiation therapy (IGRT) that monitors intra-fraction motion using X-ray imaging rather than magnetic resonance imaging (MRI). Detected anatomical variations can then either be compensated for, via patient repositioning and/or treatment modification, or the current treatment can be aborted.

In some embodiments, a higher-quality set-up scan is performed at the beginning of the patient breath-hold, for example via cone-beam computed tomography (CBCT), while digital tomosynthesis (DTS) is employed during the remainder of the breath-hold to monitor intra-fraction motion. Unlike MRI-based IGRT, according to the embodiments, such intra-fraction motion is monitored during a breath-hold within a three-dimensional (3D) region that encompasses the planning target volume. Consequently, intra-fraction motion can be monitored within a region that includes all of the planning target volume, rather than within a single two-dimensional (2D) slice of the planning target volume. In addition, to generate higher quality 3D imaging of the planning target volume after treatment has begun during the breath hold, 3D image data acquired prior to the beginning of treatment, i.e., via the CBCT scan, is modified with 3D imaging data acquired after the treatment has begun, i.e., via the DTS scan.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
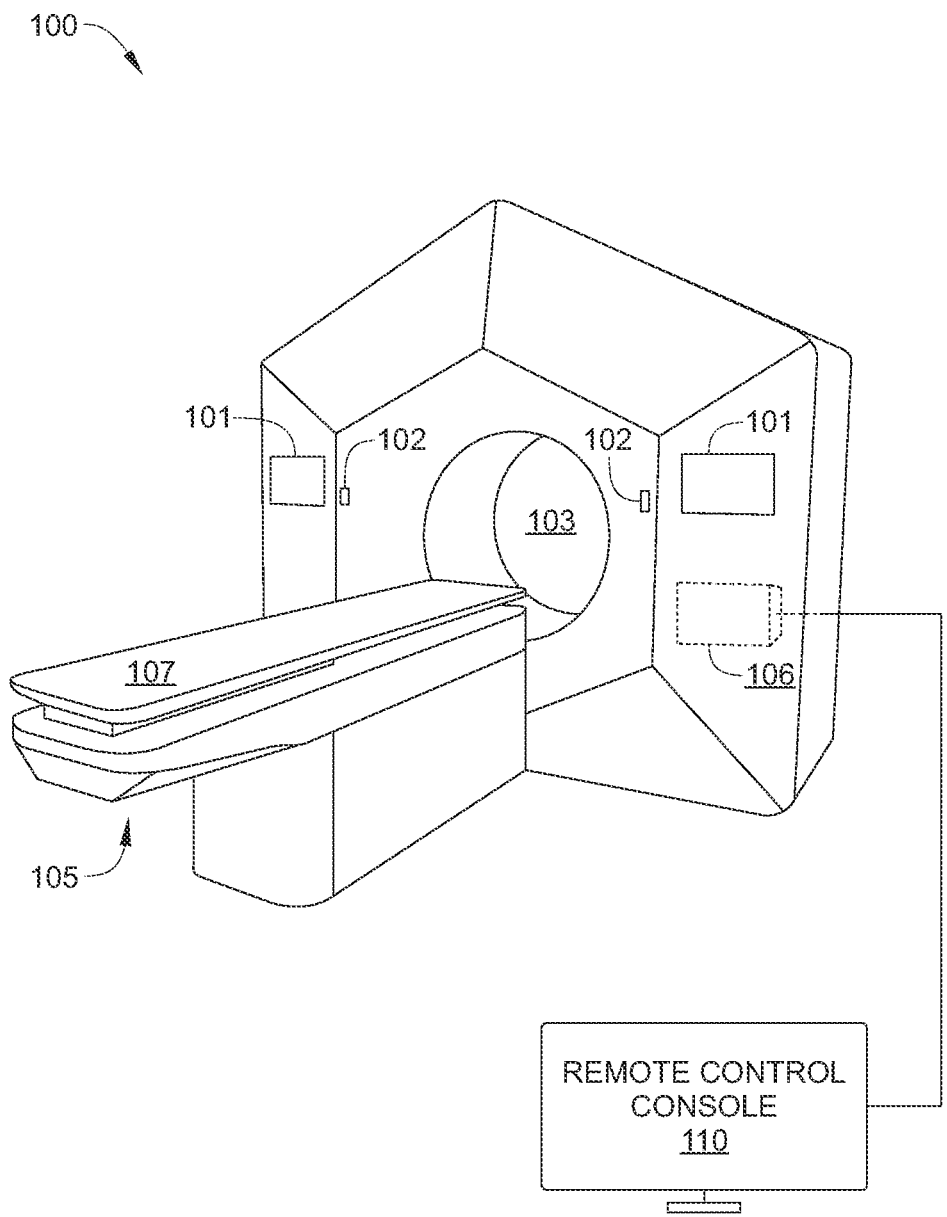
FIG. 1 is a perspective view of a radiation therapy system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Image guided radiation therapy (IGRT) is used to treat tumors in areas of the body that are subject to voluntary movement, such as the lungs, or involuntary movement, such as organs affected by peristalsis. IGRT involves the use of an imaging system to view target tissues (also referred to as the "target volume") while radiation treatment is delivered thereto. In IGRT, image-based coordinates of the target volume from a previously determined treatment plan are compared to image-based coordinates of the target volume determined during the application of the treatment beam. In this way, motion or deformation of the target volume relative to the radiation therapy system can be detected, and the patient's position and/or the treatment beam can be adjusted to more precisely target the radiation dose to the tumor.

In some conventional IGRT radiation systems, motion of soft tissues is detected during application of the treatment beam via fiducial markers, such as gold seeds. However, the use of fiducial markers has numerous drawbacks, particularly the invasive surgical procedures required for placement of the markers. Specifically, the laproscopic insertion of fiducial markers requires additional time and clinical resources, such as an operating room, anesthesia, antibiotics, and the participation of numerous additional medical specialists.

Alternatively in some conventional IGRT radiation systems, motion of soft tissues is detected during application of the treatment beam via magnetic resonance imaging (MRI). However, MRI-based IGRT also has drawbacks. First, MRI-based IGRT systems are generally larger, more complex, and more expensive than radiation therapy systems that employ X-ray imaging. Second, detecting motion or deformation of the target volume via MRI generally involves monitoring images associated with a 2D slice that passes through the target volume. As a result, target volume motion or deformation that occurs anywhere outside of (or perpendicular to) the 2D slice being monitored is difficult to detect, which can significantly impact the accuracy of the radiation dose being applied.

In light of the above, there is a need in the art for improved systems and techniques for ensuring a target volume remains properly positioned for treatment in a radiation therapy system while a treatment beam is delivered to the target volume. According to various embodiments described herein, a radiation system is configured to detect intra-fraction motion without fiducial markers and in near-real time using X-ray imaging techniques. One such embodiment is illustrated in FIG. 1.

FIG. 1 is a perspective view of a radiation therapy system 100, according to one or more embodiments of the present disclosure. Radiation therapy (RT) system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID) (not shown for clarity). By way of example, radiation therapy system 100 is described herein configured with a circular gantry.

Generally, RT system 100 is capable of kV imaging of a target volume during application of an MV treatment beam, so that an IGRT process can be performed using X-ray imaging rather than MRI. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
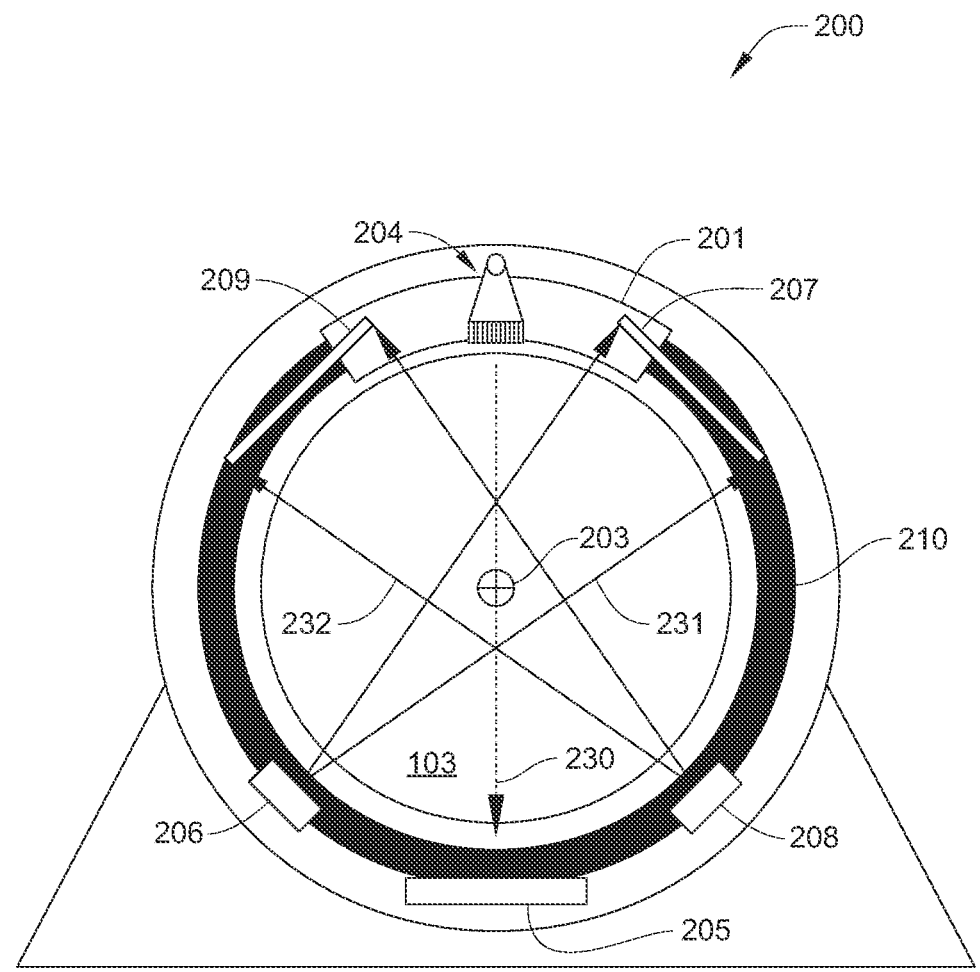
FIG. 2 schematically illustrates a gantry of the radiation therapy system of FIG. 1, according to various embodiments of the current disclosure.

FIG. 2 schematically illustrates a drive stand 200 and gantry 210 of RT system 100, according to various embodiments of the current disclosure. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, a first imaging X-ray source 206, a first X-ray imager 207, a second imaging X-ray source 208, and a second X-ray imager 209. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons) and EPID 205 is configured to acquire X-ray images with treatment beam 230. First imaging X-ray source 206 is configured to direct a conical beam of X-rays, referred to herein as imaging X-rays 231, through an isocenter 203 of RT system 100 to first X-ray imager 207. Similarly, second imaging X-ray source 208 is configured to direct a conical beam of X-rays, referred to herein as imaging X-rays 232, through isocenter 203 of RT system 100 to second X-ray imager 209. Isocenter 203 typically corresponds to the location of the target volume to be treated. First X-ray imager 207 receives imaging X-rays 231 and generates suitable projection images therefrom, and second X-ray imager 209 receives imaging X-rays 232 and generates suitable projection images therefrom. According to certain embodiments, such projection images can then be employed to construct or update portions of imaging data for a digital volume that corresponds to a 3D region that includes the target volume. In the embodiments, cone-beam computed tomography (CBCT) and digital tomosynthesis (DTS) can be used to process the projection images generated by first X-ray imager 207 and second X-ray imager 209.

In the embodiment illustrated in FIG. 2, first X-ray imager 207 and second X-ray imager 209 are depicted as planar devices. In other embodiments, first X-ray imager 207 and/or second X-ray imager 209 can have a curved configuration. In addition, in the embodiment illustrated in FIG. 2, RT system 100 includes two X-ray imagers and corresponding imaging X-ray sources. In other embodiments, RT system 100 can include three or more X-ray imagers and corresponding imaging X-ray sources, which further facilitates detection of intra-fraction motion in near-real time using X-ray imaging techniques.

In different embodiments, LINAC 204, EPID 205, first imaging X-ray source 206, first X-ray imager 207, second imaging X-ray source 208, and second X-ray imager 209 can be arranged in various configurations. One such embodiment is described below in conjunction with FIGS. 3A and 3B.

Figure 3A:
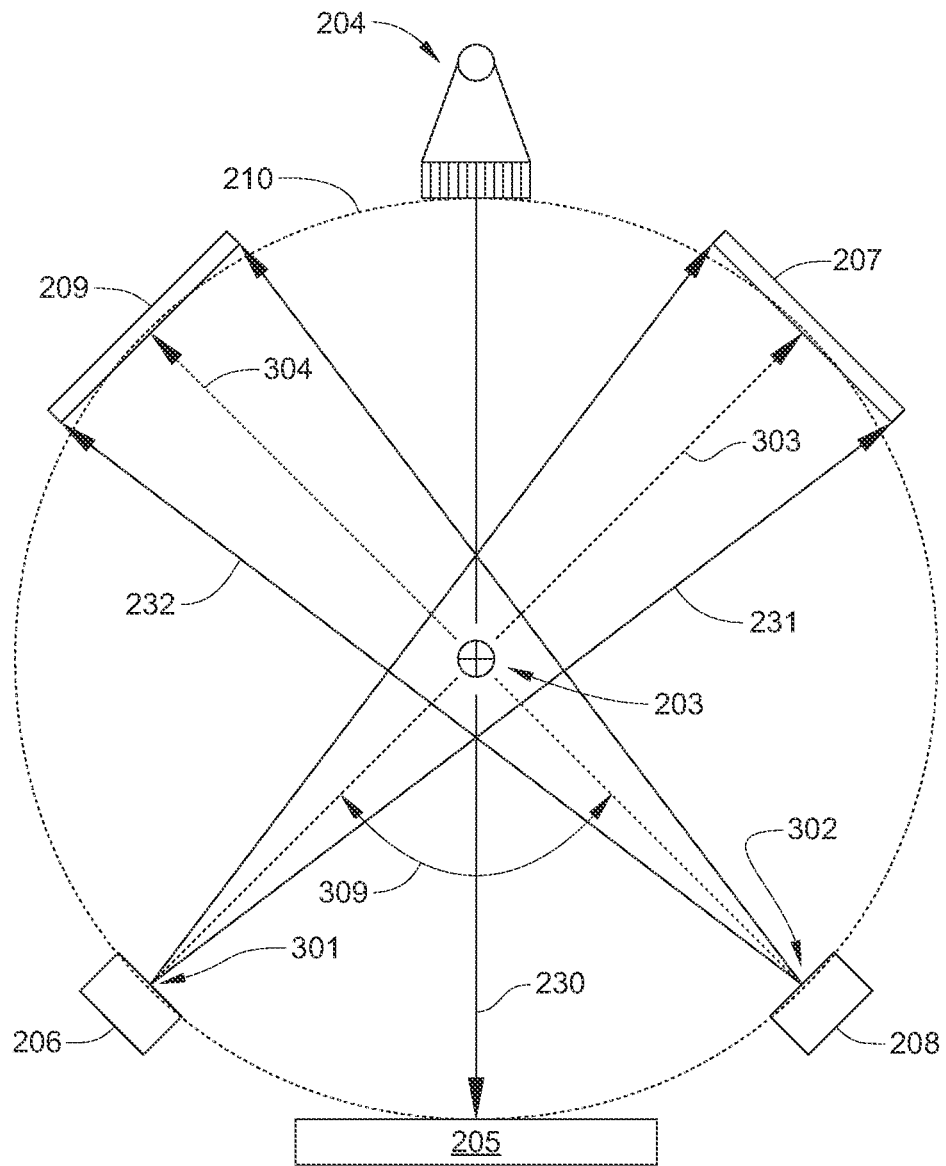
FIGS. 3A and 3B schematically illustrates X-ray generating and imaging components mounted on the gantry of FIG. 2, according to various embodiments of the current disclosure.

FIG. 3A schematically illustrates X-ray generating and imaging components mounted on gantry 210, according to various embodiments of the current disclosure. For clarity, gantry 210 is depicted as a single dashed line in FIGS. 3A and 3B. As shown, LINAC 204 is positioned to direct treatment beam 230 through isocenter 203 of RT system 100 to EPID 205. In addition, first X-ray source 206 is positioned to direct imaging X-rays 231 from a source point 301 associated with first X-ray source 206 toward first X-ray imager 207, and second X-ray source 208 is positioned to direct imaging X-rays 232 from a source point 302 associated with second X-ray source 208 toward second X-ray imager 209. In the embodiments illustrated in FIGS. 3A and 3B, first X-ray source 206 and second X-ray source 208 are positioned symmetrically with respect to LINAC 204 and EPID 205. In other embodiments, first X-ray source 206 and second X-ray source 208 can be positioned asymmetrically on gantry 210 with respect to LINAC 204 and EPID 205. Similarly, first X-ray imager 207 and second X-ray imager 209 can be positioned on gantry 210 symmetrically or asymmetrically with respect to LINAC 204 and EPID 205.

The projection images generated by first X-ray source 206 and second X-ray source 208 are used to construct imaging data for a digital volume of patient anatomy within a 3D region that includes the target volume. Alternatively or additionally, such projection images can be used to update portions of an existing imaging data for the digital volume corresponding to the 3D region. One embodiment of such a digital volume is described below in conjunction with FIG. 4.

Figure 4:
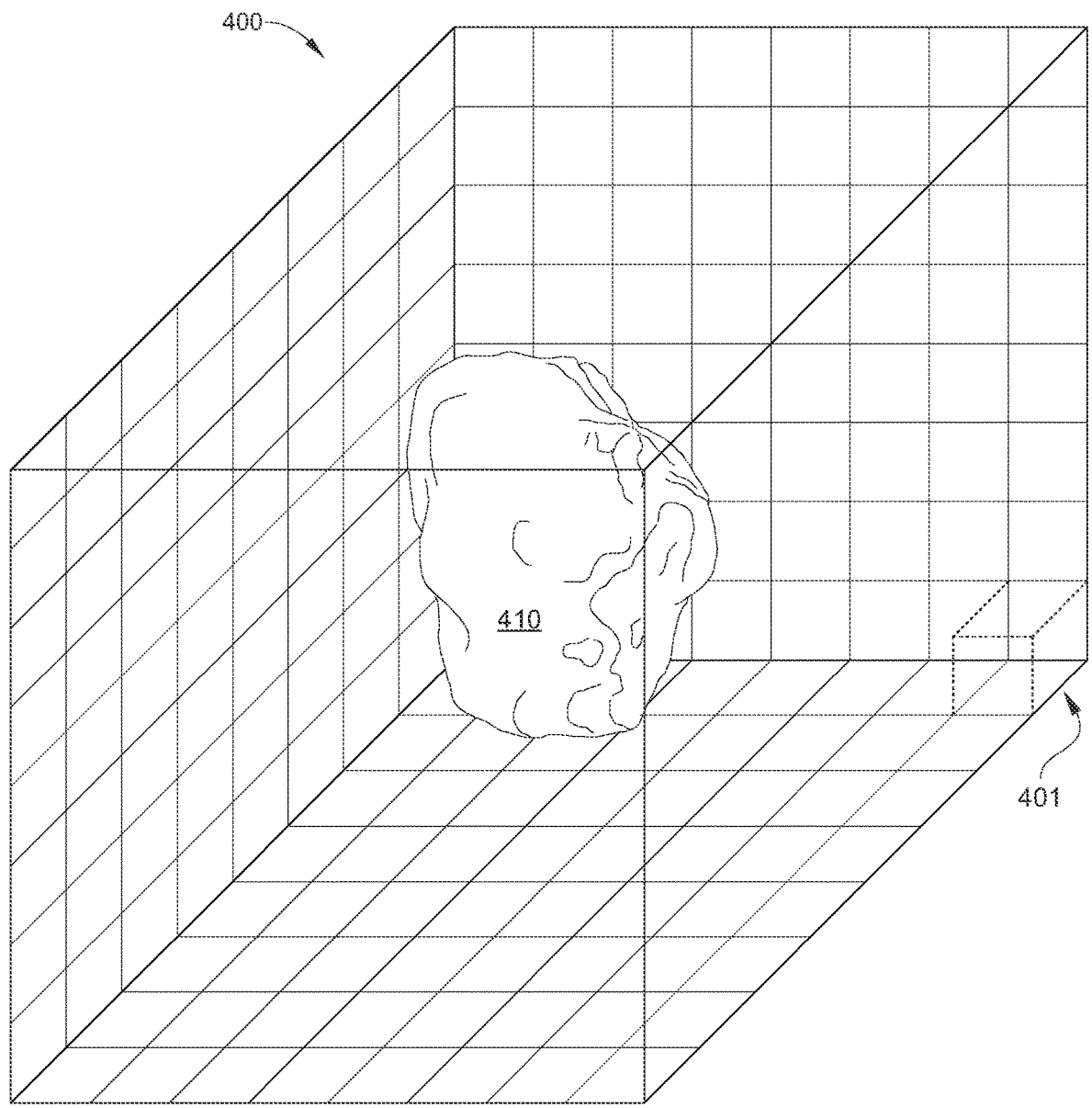
FIG. 4 schematically illustrates a digital volume that is constructed based on projection images generated by a first X-ray source and a second X-ray source, according to various embodiments of the current disclosure.

FIG. 4 schematically illustrates a digital volume 400 that is constructed based on projection images generated by first X-ray source 206 and second X-ray source 208, according to various embodiments of the current disclosure. Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by embodiments of the invention.

According to various embodiments described below, image information associated with each voxel 401 of digital volume 400 is constructed via projection images generated by first X-ray source 206 and second X-ray source 208 via a CBCT process. For example, such a CBCT process can be employed immediately prior to delivering treatment beam 230 to target volume 410, so that the location and shape of target volume 410 can be confirmed before treatment begins. In addition, according to various embodiments described below, image information associated with some or all of voxels 401 of digital volume 400 is updated via projection images generated by first X-ray source 206 and second X-ray source 208 via a DTS process. For example, such a DTS process can be employed after a portion of a planned treatment has begun and before the planned treatment has completed. In this way, the location and shape of target volume 410 can be confirmed while the treatment is underway. Thus, if a sufficient portion of the target volume 410 is detected to be extending outside a threshold region (for example due to respiration, peristalsis, loss of breath hold, etc.), the treatment can either be aborted or modified. In such an instance, modification of the treatment can be accomplished by adjusting patient position and/or the treatment beam. In some embodiments, modification of the treatment is performed between treatment arcs. In other embodiments, modification of the treatment is performed during a treatment arc, while the treatment beam is being applied.

During use, treatment beam 230 typically generates a large amount of scattered radiation in all directions, including that emanating from the patient, treatment table, and machine components, as well as that leaking from LINAC 204. As a result, a large amount of MV scatter can be incident on first X-ray imager 207 and second X-ray imager 209. In some instances, the amount of such X-ray scatter can exceed the magnitude of imaging X-rays 231 and imaging X-rays 232 that are incident on first X-ray imager 207 and second X-ray imager 209. Accordingly, in some embodiments, time-domain interleaving of treatment beam 230 with imaging X-rays 231 and imaging X-rays 232 can be employed to reduce or eliminate interference from X-ray scatter of treatment beam 230 with the detection of imaging X-rays 231 and imaging X-rays 232. In such embodiments, imaging X-rays 231, imaging X-rays 232, and treatment beam 230 are pulsed or otherwise intermittently activated, so that when imaging X-rays 231 and imaging X-rays 232 are directed to target volume 410, treatment beam 230 is not being delivered to target volume 410. That is, in such embodiments, imaging X-rays 231 and imaging X-rays 232 are gated off when treatment beam 230 is on.

In some embodiments, a typical kV pulse is about 10 ms (millisecond) in duration, with images acquired approximately every 30 ms. In such an embodiment, a typical MV pulse of treatment beam 230 can be significantly shorter in duration than the above-described kV pulses, for example 5 μs (microsecond) in duration. In such an embodiment, pulses of treatment beam 230 can be delivered about every 1-10 ms when imaging X-rays 231 and imaging X-rays 232 are gated off. Therefore, under such circumstances, if imaging X-rays 231 and imaging X-rays 232 are delivered simultaneously with MV pulses of treatment beam 230, several MV pulses of treatment beam 230 could be delivered within a kV pulse.

In some embodiments, a series of multiple MV pulses of treatment beam 230 is delivered between each kV pulse of imaging X-rays 231 and imaging X-rays 232. In one such embodiment, in which kV pulses are about 10 ms in duration, X-ray images are acquired approximately every 30 ms, and MV pulses of treatment beam 230 are about 1 to 10 μs in duration, there is a 20 ms window between kV pulses for delivery of MV pulses of treatment beam 230. Alternatively, in some embodiments, the duration of the kV pulses of imaging X-rays 231 and imaging X-rays 232 is shortened and/or the separation of the MV pulses of treatment beam 230 in time is lengthened, so that a kV imaging pulse fits between a series of multiple MV pulses. For example, in an embodiment in which an X-ray image is acquired in about 1 to 5 ms, imaging can be executed between certain MV pulses of treatment beam 230.

Figure 3B:
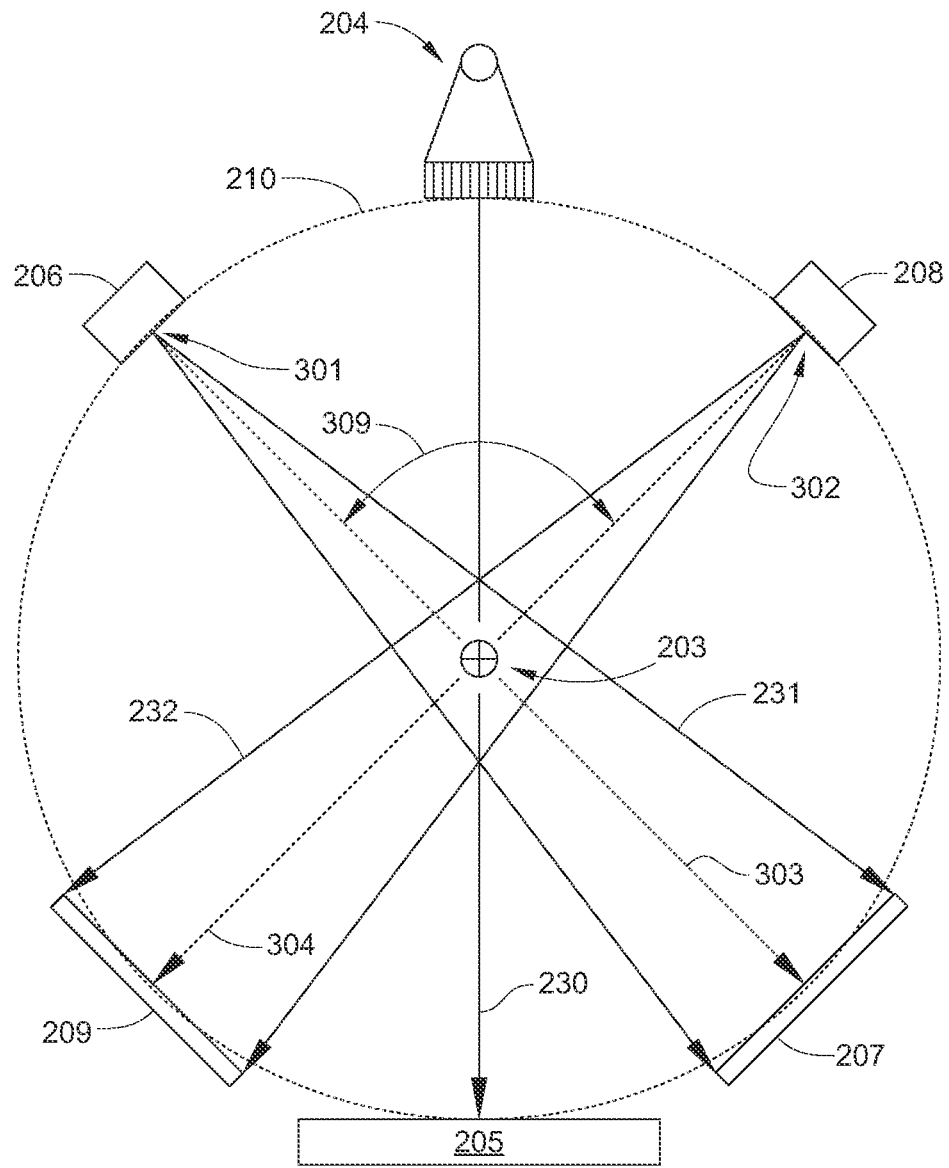

Returning to the embodiment illustrated in FIGS. 3A and 3B, first X-ray source 206 and second X-ray source 208 are positioned so that a first imaging beam path 303 (starting at source point 301 and ending at first X-ray imager 207) is separated from a second imaging beam path 304 (starting at source point 302 and ending at second X-ray imager 209) by an imager separation angle 309. In various embodiments, imager separation angle 309 can be as small as about 30 degrees and as large as about 120 degrees. In some embodiments, to provide enhanced localization accuracy in a direction normal to treatment beam 230, RT system 100 is configured with an imager separation angle 309 that is significantly smaller than 90 degrees. In some embodiments, to provide enhanced isotropic resolution, RT system 100 is configured with an imager separation angle 309 that is 90 degrees, as shown in FIGS. 3A and 3B.

In the embodiment illustrated in FIGS. 3A and 3B, first imaging beam path 303 is perpendicular to second imaging beam path 304. Further, first imaging beam path 303 and second imaging beam path 304 may each pass through isocenter 203. Thus, imager separation angle 309 between first imaging beam path 303 and second imaging beam path 304 is 90 degrees. In such embodiments, image information generated for constructing or updating voxels 401 of digital volume 400 can generally be collected over a shorter arc of rotation of gantry 210 than when first X-ray source 206 and second X-ray source 208 are positioned so that imager separation angle 309 is smaller or larger than 90 degrees.

For example, in the embodiment illustrated in FIGS. 3A and 3B, first X-ray imager 207 and second X-ray imager 209 can generate a threshold imaging data set when gantry 210 rotates through an acquisition arc angle of about 30 degrees, where the threshold imaging data set is a set of imaging data for populating or updating a portion of digital volume 400 that is sufficiently large and of sufficient accuracy that the current shape and position of target volume 410 can be accurately determined to within a required tolerance. In such embodiments, imaging data that are generated by first X-ray imager 207 and second X-ray imager 209 in the form of projection images a DTS process is performed thereon. By contrast, in embodiments in which imager separation angle 309 is greater than or less than 90 degrees, gantry rotation of more than 30 degrees may be needed for first X-ray imager 207 and second X-ray imager 209 to generate the threshold imaging data set. Further, in a conventional RT system that includes a single kV X-ray source and corresponding kV X-ray imager, gantry rotation of 60 degrees or more may be needed for the single kV X-ray imager to generate the threshold imaging data set. Because gantry rotational velocity during treatment is typically limited to a small number of rotations per minute (e.g., 2-5 rotations per minute), rotation of a gantry through 60 degrees of arc can be a prohibitively long time for receiving feedback for the current position and shape of target volume 410, e.g., several seconds. Instead, in the embodiment illustrated in FIGS. 3A and 3B, such feedback imaging can be provided in near-real time, e.g., after about one second of gantry rotation. One instance of gantry rotation is illustrated in FIG. 5.

Figure 5:
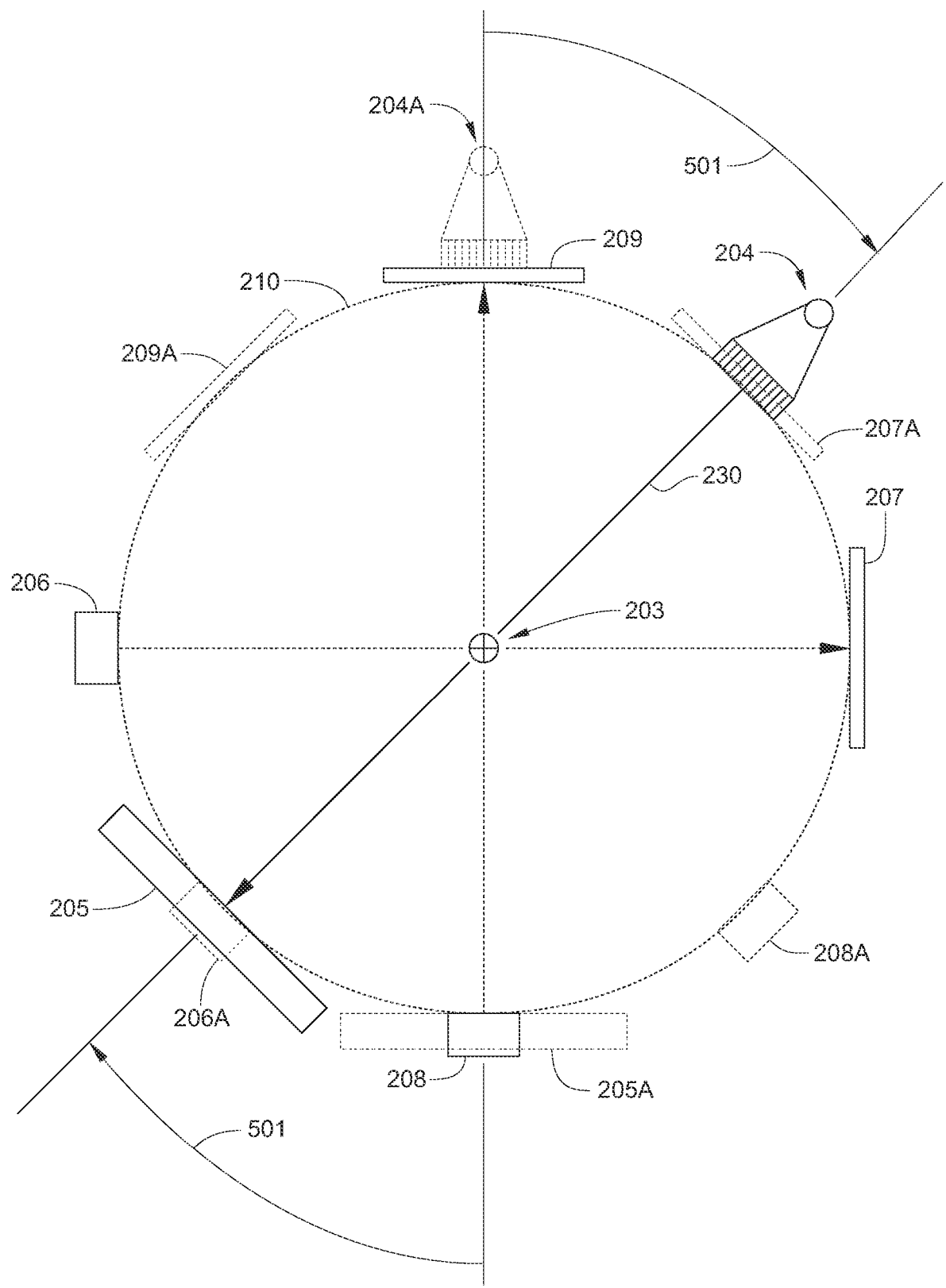
FIG. 5 schematically illustrates X-ray generating and imaging components that are mounted on a gantry after the gantry rotates 45 degrees, according to various embodiments of the current disclosure.

FIG. 5 schematically illustrates X-ray generating and imaging components that are mounted on gantry 210 after gantry 210 rotates 45 degrees, according to various embodiments of the current disclosure. As shown, LINAC 204, EPID 205, first imaging X-ray source 206, first X-ray imager 207, second imaging X-ray source 208, and second X-ray imager 209 rotate together about isocenter 203. In the instance illustrated in FIG. 5, gantry 210, and the above components mounted thereon, have rotated through an acquisition arc angle 501 from an initial rotational position to a current rotational position, where the acquisition arc angle 501 is 45 degrees. For reference, an initial position 204A of LINAC 204, an initial position 205A of EPID 205, an initial position 206A of first imaging X-ray source 206, an initial position 207A of first X-ray imager 207, an initial position 208A of second imaging X-ray source 208, and an initial position 209A of second X-ray imager 209 are also shown in FIG. 5 (dashed lines).

It is noted that, because RT system 100 includes two imaging X-ray sources and corresponding X-ray imagers, the effective tomographic angle of acquisition arc angle 501 is approximately doubled. For a typical CBCT acquisition, the tomographic angle through which gantry 210 rotates during acquisition of image data is ideally sufficiently large so that at least about 180 degrees of rays intersect, with sufficient sampling density, each pixel of a 2D image being generated from a digital volume in the reconstructed field of view. For example, in some instances, the minimum rotation for a complete CBCT scan is considered 180 degrees plus the kV fan angle (typically about 30 degrees), which indicates a minimum rotation of about 210 degrees. Thus, because RT system 100 includes two (or more) imaging X-ray sources and corresponding X-ray imagers, the CBCT requirement for approximately 180 degrees of rays intersecting each pixel can be achieved with an acquisition arc angle 501 of approximately 90 degrees. Furthermore, in embodiments in which RT system 100 includes three imaging X-ray sources and corresponding X-ray imagers, the effective tomographic angle of acquisition arc angle 501 is approximately tripled, and the CBCT requirement for approximately 180 degrees of rays intersecting each pixel can be achieved with an acquisition arc angle 501 of approximately 60 degrees.

In a similar vein, DTS acquisitions performed by RT system 100 also benefit from the multiple imaging X-ray sources and corresponding X-ray imagers included in RT system 100. According to various embodiments, DTS acquisitions, also referred to as "partial arc CBCT acquisitions," are employed to generate image data for digital volume 400 via a reduced acquisition arc angle 501. Specifically, DTS acquisitions, taken across acquisition arc angles 501 of between about 5 and about 45 degrees, can generate sufficiently accurate data for digital volume 400 that motion and deformation of target volume 410 can be reliably detected while a treatment beam is being applied to target volume 410. It is noted that, because significant time is required to rotate gantry 210 through larger acquisition arc angles 501, there is a trade-off between acquiring sufficient image data for higher-quality images and generating such images with sufficient temporal resolution. However, according to various embodiments described herein, DTS acquisitions, employed in conjunction with an RT system that includes multiple imaging X-ray sources and X-ray imagers, can provide sufficient temporal resolution and localization accuracy of target volume 410 for the IGRT process.

Because acquisition arc angle 501 is an acquisition parameter that can be varied depending on a particular IGRT process being performed, in some embodiments, acquisition arc angle 501 can be selected based on multiple factors. Such factors include how much tomographic information is required for accurate localization of target volume 410, how frequently updated localization information is required, patient-specific characteristics (such as ability to hold breath), size and location of the anatomical target, and the like.

In some embodiments, imager separation angle 309 is selected based on factors not directly related to imaging. For example, to accommodate the positioning of other components on gantry 210, first imaging X-ray source 206, first X-ray imager 207, second imaging X-ray source 208, and second X-ray imager 209 are positioned differently relative to LINAC 204 and EPID 205 than illustrated in FIGS. 3A, 3B, and 5. One such embodiment is illustrated in FIG. 6.

Figure 6:
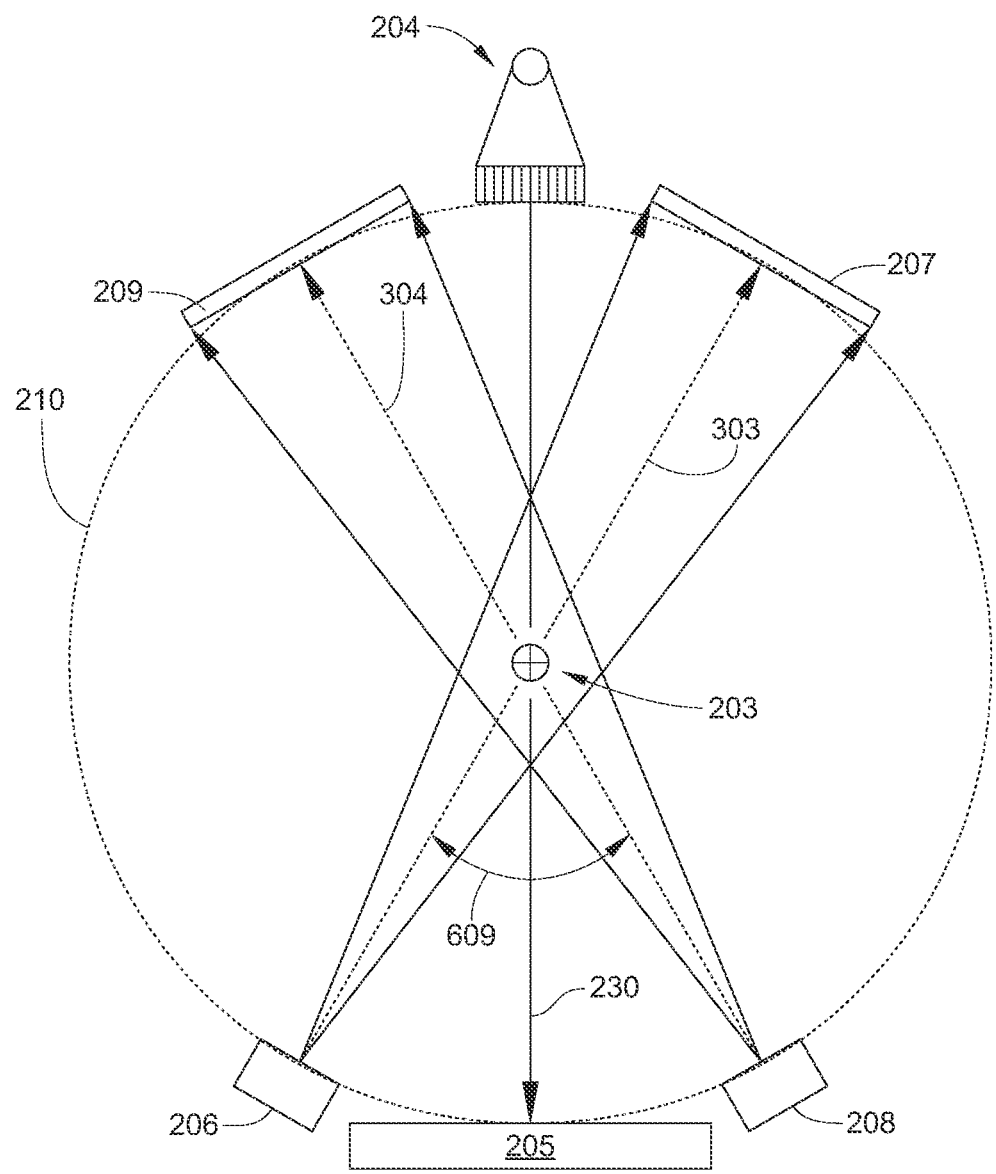
FIG. 6 schematically illustrates X-ray generating and imaging components mounted on a gantry, according to various embodiments of the current disclosure.

FIG. 6 schematically illustrates X-ray generating and imaging components mounted on gantry 210, according to various embodiments of the current disclosure. As shown, first imaging X-ray source 206 is mounted on gantry 210 proximate to and on a first side of EPID 205, while second imaging X-ray source 208 is mounted on gantry 210 proximate to and on a second side of EPID 205. As a result, an imager separation angle 609 between first imaging beam path 303 and second imaging beam path 304 is less than 90 degrees.

In some embodiments, RT system 100 includes one or more imaging X-ray sources that are positioned on gantry 210 in a half-fan configuration for generating imaging X-rays. Alternatively or additionally, in some embodiments, RT system 100 includes one or more imaging X-ray sources that are positioned on a gantry in a half-fan configuration for generating imaging X-rays. One such embodiment is illustrated in FIG. 7.

Figure 7:
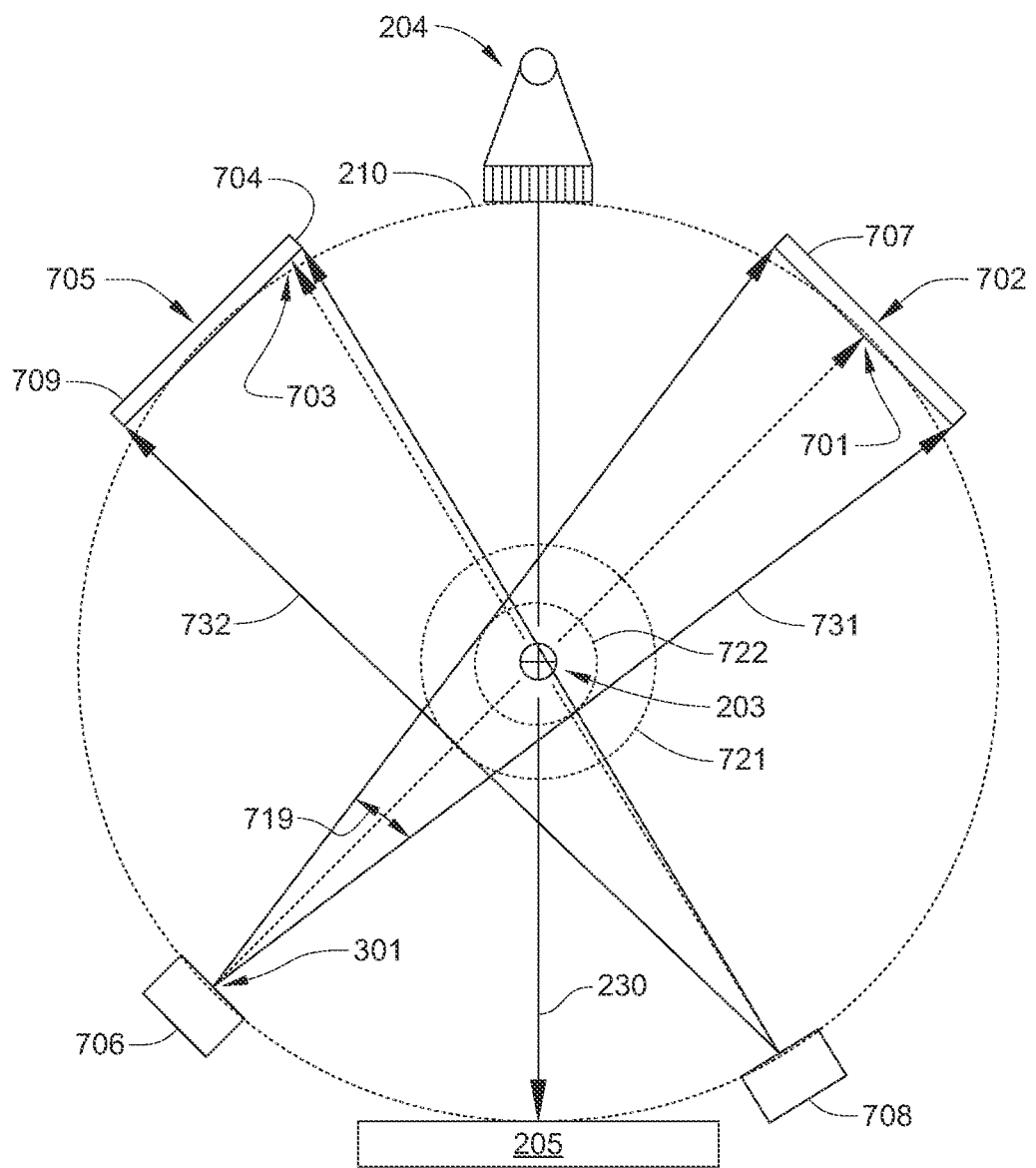
FIG. 7 schematically illustrates X-ray generating and imaging components mounted on a gantry, according to various other embodiments of the current disclosure.

FIG. 7 schematically illustrates X-ray generating and imaging components mounted on gantry 210, according to various other embodiments of the current disclosure. As shown, a first imaging X-ray source 706 and a first X-ray imager 707 are positioned on a gantry 210 in a full-fan configuration for generating imaging X-rays 731. That is, first X-ray imager 707 is positioned on gantry 210 so that a piercing point 701 of first X-ray imager 707 is at or near a center point 702 of first X-ray imager 707, where the piercing point of an X-ray imager is defined as the point on the imager that intersects with a line segment starting from an X-ray source and extending through the rotation isocenter (i.e., isocenter 203). In addition, a second imaging X-ray source 708 and a second X-ray imager 709 are positioned on gantry 210 in a half-fan configuration for generating imaging X-rays 732. That is, second X-ray imager 709 is positioned on gantry 210 so that a piercing point 703 of imaging X-rays 732 is at or near an edge 704 of second X-ray imager 709, rather than at or near a center point 705 of second X-ray imager 709. Thus, in the embodiment illustrated in FIG. 7, first X-ray imager 707 and second X-ray imager 709 can be positioned asymmetrically on gantry 210 with respect to LINAC 204 and EPID 205.

Full-fan (or "centered-detector") configurations of an imaging X-ray source and X-ray imager have the advantage of enabling the use of a shorter acquisition arc angle (such as acquisition arc angle 501 shown in FIG. 5). Thus, use of a full-fan configuration can reduce acquisition time, but results in a significantly smaller field of view than half-fan configurations. By way of illustration, a full-fan field of view 721 for first imaging X-ray source 706 and first X-ray imager 707 and a half-fan field of view 722 for second imaging X-ray source 707 and second X-ray imager 709 are shown in FIG. 7. According to various embodiments, use of a full-fan configuration in conjunction with multiple imaging X-ray sources and corresponding X-ray imagers can further reduce acquisition time. In such embodiments, acquisition time can be minimized or otherwise reduced by selecting an imager separation angle (such as imager separation angle 309 shown in FIGS. 3A and 3B) that is equal to (180+an X-ray fan angle 719)/2. The above-described full-fan configuration can be advantageously employed in CBCT acquisitions when adequate field of view can be produced. In addition, in intra-fraction DTS acquisitions, a large field of view is generally not needed. Thus, the above-described full-fan configuration can also be advantageously employed in intra-fraction DTS acquisitions, since acquisition times are reduced. As a result, faster feedback of the current location and deformation of a target volume during treatment is enabled.

Half-fan (or "offset-detector") configurations of an imaging X-ray source and X-ray imager have the advantage of a larger resultant field of view, but generally require a larger acquisition arc angle. Thus, use of a half-fan configuration can increase acquisition time and the associated latency in detecting motion or deformation of a target volume. However, according to various embodiments, the use of multiple imaging X-ray sources and corresponding X-ray imagers can further reduce acquisition time. For example, in an embodiment in which RT system 100 has a half-fan configuration and an imager separation angle 309 that is 90 degrees or less, for acquiring a complete CBCT data set, acquisition arc angle 501 is reduced from 360 degrees to 180 plus the imager separation angle 309. In an embodiment in which RT system 100 has a half-fan configuration and an imager separation angle 309 that is greater than 90 degrees, for acquiring a complete CBCT data set, acquisition arc angle 501 is reduced from 360 degrees to 360 minus the imager separation angle 309.

In some embodiments, an adjustable collimator (not shown) is disposed between the imaging X-ray source and the X-ray imager. In such embodiments, a full-fan configuration and a half-fan configuration of an imaging X-ray source and X-ray imager is selected based on the position of the collimator. For example, in a full-fan configuration, the adjustable collimator is positioned to allow imaging X-rays from the imaging X-ray source to be incident on all or substantially all of the X-ray imager. By contrast, in a half-fan configuration, the adjustable collimator is positioned to allow imaging X-rays from the imaging X-ray source to be incident on approximately one half of the X-ray imager.

In the embodiment illustrated in FIG. 7, RT system 100 includes one imaging X-ray source and a corresponding X-ray imager that are positioned in a half-fan configuration and one imaging X-ray source and a corresponding X-ray imager that are positioned in a full-fan configuration. In other embodiments, both imaging X-ray sources and corresponding X-ray imagers are positioned in a half-fan configuration. In other embodiments, both imaging X-ray sources and corresponding X-ray imagers are positioned in a full-fan configuration. In yet other embodiments, one or more of the imaging X-ray sources and corresponding X-ray imagers can be selectively deployed in either a half-fan configuration or a full-fan configuration. One such embodiment is illustrated in FIG. 8.

Figure 8:
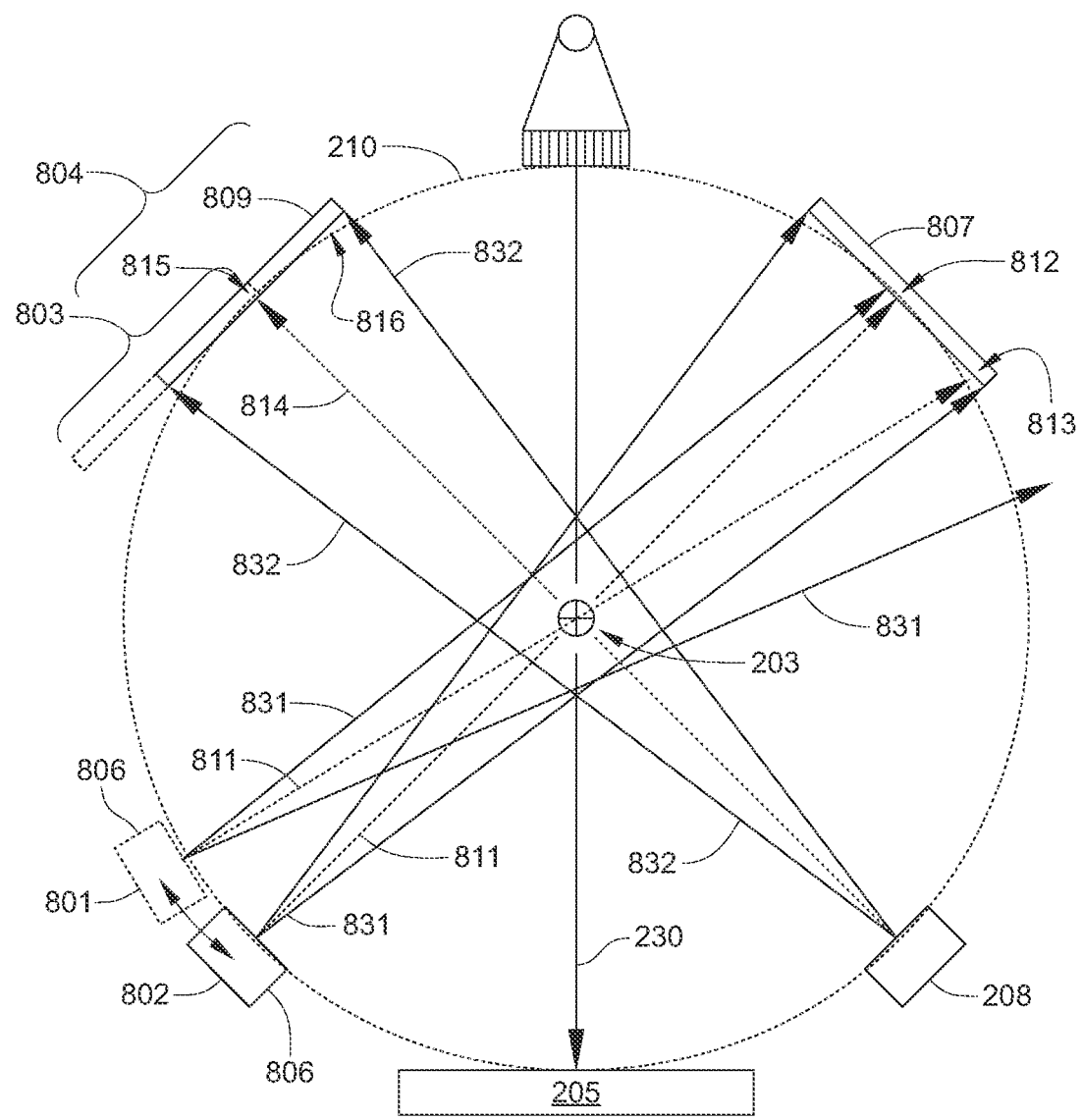
FIG. 8 schematically illustrates X-ray generating and imaging components mounted on gantry, according to various other embodiments of the current disclosure.

FIG. 8 schematically illustrates X-ray generating and imaging components mounted on gantry 210, according to various other embodiments of the current disclosure. As shown, a first imaging X-ray source 806 is configured to be adjustable between two positions: a half-fan position 801 and a full-fan position 802. As shown, motion (for example, tilting and/or laterally shifting) of first imaging X-ray source 806 between half-fan position 801 (broken lines) and full-fan position 802 results in a piercing vector 811 of imaging X-rays 831 that passes through isocenter 203 shifting in location on a corresponding first X-ray imager 807. That is, in full-fan position 802, piercing vector 811 is directed to approximately a center point 812 of first X-ray imager 807, while in half-fan position 801, piercing vector 811 is directed to an edge region 813 of first X-ray imager 807. Thus, in the embodiment illustrated by first imaging X-ray source 806 and first X-ray imager 807, motion of X-ray source 806 enables selection between half-fan position 801 and full-fan position 802. Motion of first imaging X-ray source 806 between half-fan position 801 and full-fan position 802 can be motorized, implemented via a pneumatic actuator, manually adjusted, or performed by any other suitable adjustment mechanism. Alternatively or additionally, an adjustable collimator (not shown) included in first imaging X-ray source 806 can be employed to select between a half-fan configuration and a full-fan configuration of first imaging X-ray source 806.

In alternative embodiments, motion of a second X-ray imager 809 between a half-fan position 803 (broken lines) and a full-fan position 804 results in a piercing vector 814 of imaging X-rays 832 that passes through isocenter 203 shifting in location on second X-ray imager 809. In such an embodiment, imaging X-rays 832 are generated by a corresponding second imaging X-ray source 808. In full-fan position 804, piercing vector 814 is directed to approximately a center point 815 of second X-ray imager 809, while in half-fan position 803, piercing vector 814 is directed to an edge region 816 of second X-ray imager 809. Motion of second X-ray imager 809 between half-fan position 803 and full-fan position 804 can be motorized, implemented via a pneumatic actuator, manually adjusted, or performed by any other suitable adjustment mechanism.

Figure 9:
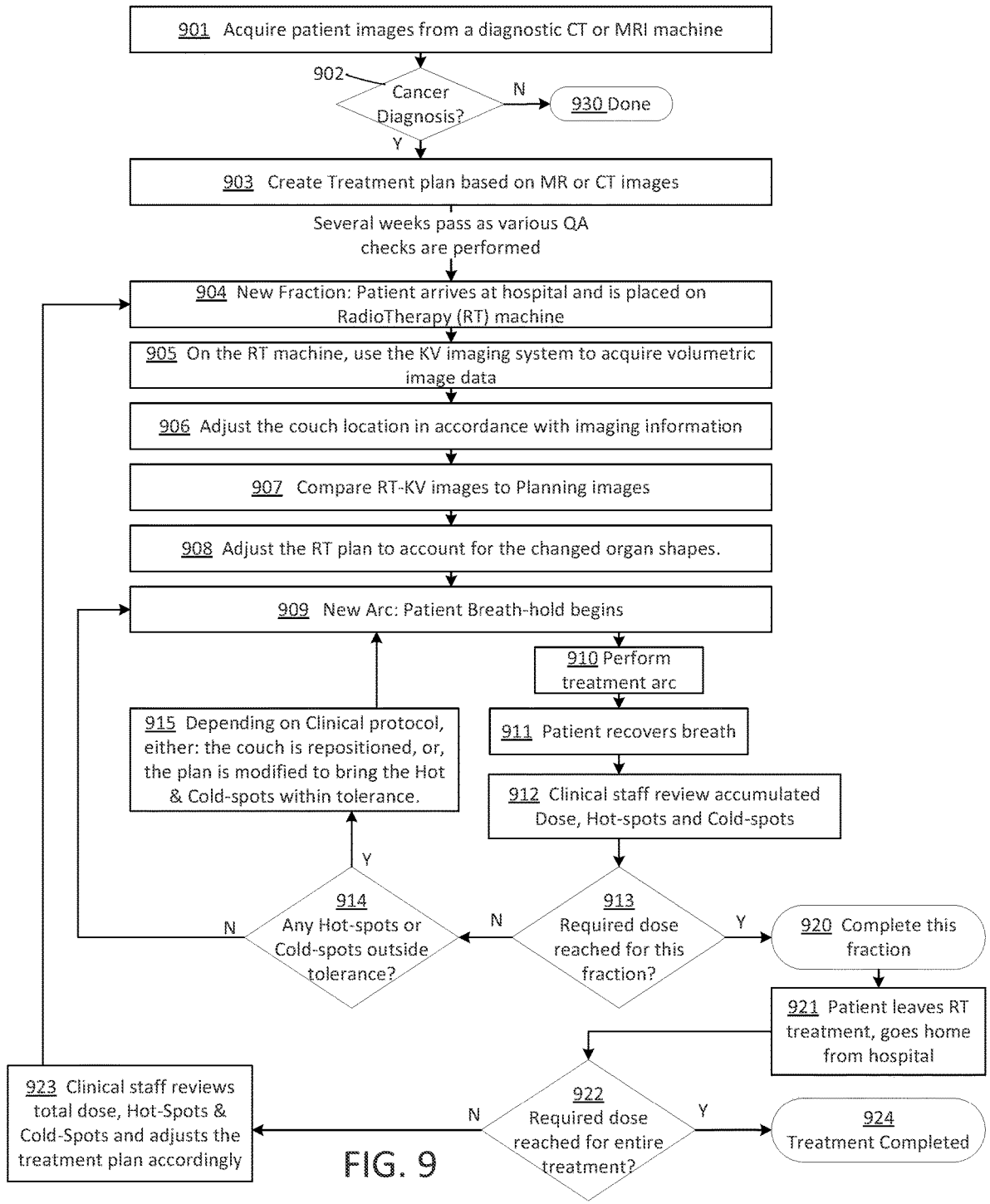
FIG. 9 sets forth a flowchart of a radiation therapy process, according to one or more embodiments of the present disclosure.

FIG. 9 sets forth a flowchart of a radiation therapy process, according to one or more embodiments of the present disclosure. The method may include one or more operations, functions, or actions as illustrated by one or more of blocks 901-930. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-8, persons skilled in the art will understand that any suitably configured radiation therapy system is within the scope of the present disclosure.

A method begins at step 901, when diagnostic volumetric (3D) image data for a digital volume 400 that includes a target volume 410 is acquired and patient images based on the diagnostic volumetric image data are generated. Typically, the diagnostic volumetric image data include image information for each voxel 401 in digital volume 400, and can be acquired from a diagnostic computed tomography (CT), CBCT, or MRI system. When produced by a CT or CBCT process, the diagnostic volumetric image data can include hundreds of distinct digital X-ray projection images of digital volume 400. In step 902, a cancer diagnosis is performed. If cancer is diagnosed, the method proceeds to step 903; if not, the method proceeds to step 930 and terminates. In step 903, a treatment plan is created based on the CT or MRI images generated in step 901. Typically, the treatment plan specifies the number of fractions (visits to a treatment facility) and the dose (including number of treatment arcs) per fraction. In addition, the treatment plan generally specifies the geometries of the tumor target, organs at risk, and orientation angles of the treatment beam. As described, if the target volume is subsequently changed in position and or shape, for example due to stomach, bladder, or colon filling, then such details of the plan can be correspondingly modified.

In step 904, performance of a fraction is initiated when the patient arrives at the treatment facility and is positioned on an RT system, such as on couch 107 of RT system 100. Steps 904 typically occurs after various QA checks are performed with respect to the treatment plan created in step 903, for example up to several weeks after step 903. In step 905, while the patient is positioned on couch 107 of RT system 100, a kV imaging system included in RT system 100 acquires volumetric image data. In some embodiments, auto-segmentation and deformable registration of the digital volume is then performed, followed by patient position adjustment (step 906). Auto-segmentation includes the delineation of target volumes and organs at risk within digital volume 400. Deformable registration adjusts contours generated in an earlier planning phase for target volume 410 and any organs at risk. The deformable registration process compensates for changes in the shape and relative location of target volume 410 and organs at risk, for example due to stomach, colon, and bladder filling, tumor shrinkage, and other factors. In step 906, the location of couch 107 is adjusted in accordance with the volumetric imaging information acquired in step 905. Thus, the current position of the patient is adjusted, when applicable, to precisely align target volume 410 with the now modified planning target volume. For example, the position of couch 107 can be automatically and/or manually adjusted to align target volume 410 with the modified planning target volume. In step 907, images of the target volume (based on the volumetric image data acquired in step 905) are compared to the planning images of the target volume acquired in step 901. In step 908, the treatment plan is adjusted to account for changes detected in certain organ shapes.

In step 909, performance of one treatment arc of the current fraction is initiated when a patient breath-hold begins. In step 910, the treatment arc is executed, in which imaging information from multiple X-ray imagers is employed during the treatment arc to detect intra-fraction motion in near-real time, according to embodiments of the disclosure. The treatment arc is performed during a single patient breath-hold. Step 910 is described in greater detail below in conjunction with FIG. 10. In step 911, the patient recovers breath, and in step 912, dosing of target volume 410 and surrounding organs at risk are calculated, and clinical staff reviews accumulated dose, hot spots, and cold spots. A "hot spot" is a portion of target volume 410 or an organ at risk that has received more than a predetermined allowable dose, while a "cold spot" is a portion of target volume 410 that has received less than a planned dose level for the current point in the treatment. It is noted that, according to embodiments of the present disclosure, step 911 is executed based on imaging information acquired during step 910 from first X-ray imager 207 and second X-ray imager 209. Typically, steps 911 and 912 are performed simultaneously, but can also be performed in series. In step 913, the determination is made whether the required dose of the target volume for the current fraction has been reached. In some embodiments, clinical staff makes such a determination, and in other embodiments, such a determination can be an automated process. If the required dose for the current fraction has been reached, the method proceeds to step 920; if the required dose for the current fraction has not been reached, the method proceeds to step 914.

In step 914, the determination is made whether any hot spots or cold spots detected in step 913 exceed a specified position and/or dosing tolerance. If such a tolerance is exceeded, the method proceeds to step 915; if not, the method returns back to step 909, and performance of the next treatment arc of the current fraction is initiated when another patient breath-hold begins. In step 915, one or more adjustments are made in response to the specified position and/or dosing tolerance being exceeding in the preceding treatment arc. In some embodiments, couch 107 is repositioned to bring the detected hot and/or cold spots within the specified tolerance. Alternatively or additionally, in some embodiments, the treatment plan is modified to bring the detected hot and/or cold spots within the specified tolerance. For example, the planned field shape and/or intensity of treatment beam 230 can be modified to compensate for the detected hot spots and/or cold spots. After such adjustments are made, the method proceeds back to step 909, and performance of the next treatment arc of the current fraction is initiated when another patient breath-hold begins. In an alternative embodiment, the adjustments performed in step 915 can be performed during execution of the treatment arc in step 910.

In step 920, which occurs upon determination that the required dose for the current fraction has been reached, the current fraction is completed. In step 921, the patient leaves the treatment facility. In step 922, the determination is made whether the specified dose for the entire treatment has been reached. If yes, the method proceeds to step 924 and the treatment is completed; if no, method proceeds to step 923. In step 923, clinical staff reviews the total dose and detected hot spots and cold spots, and adjusts the treatment plan accordingly. The method then returns to 904 and the performance of the next fraction of treatment is initiated when the patient again arrives at the treatment facility.

Figure 10:
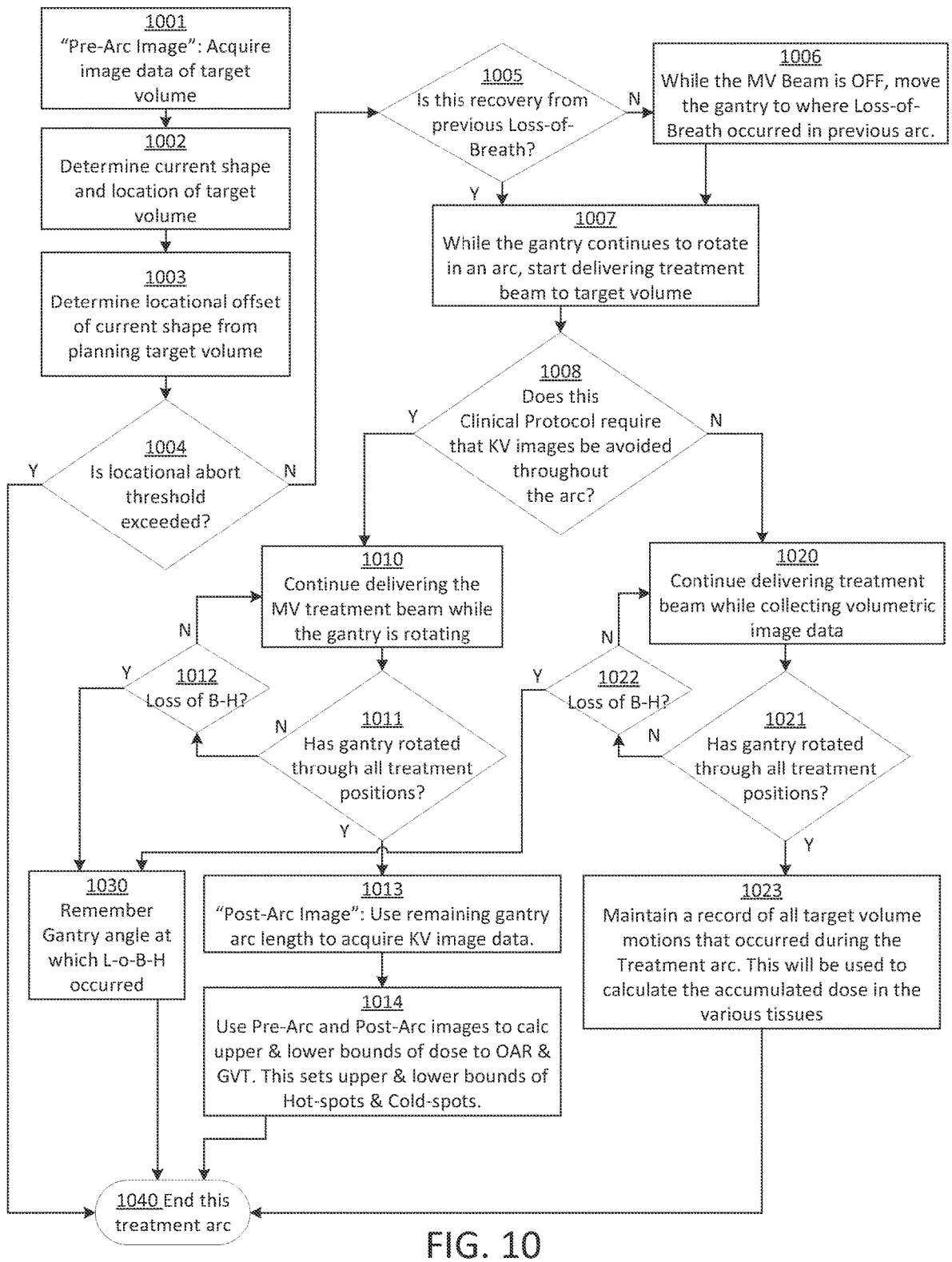
FIG. 10 sets forth a flowchart of an example computer-implemented method of radiation therapy, according to one or more embodiments of the present disclosure.
Figure 11A:
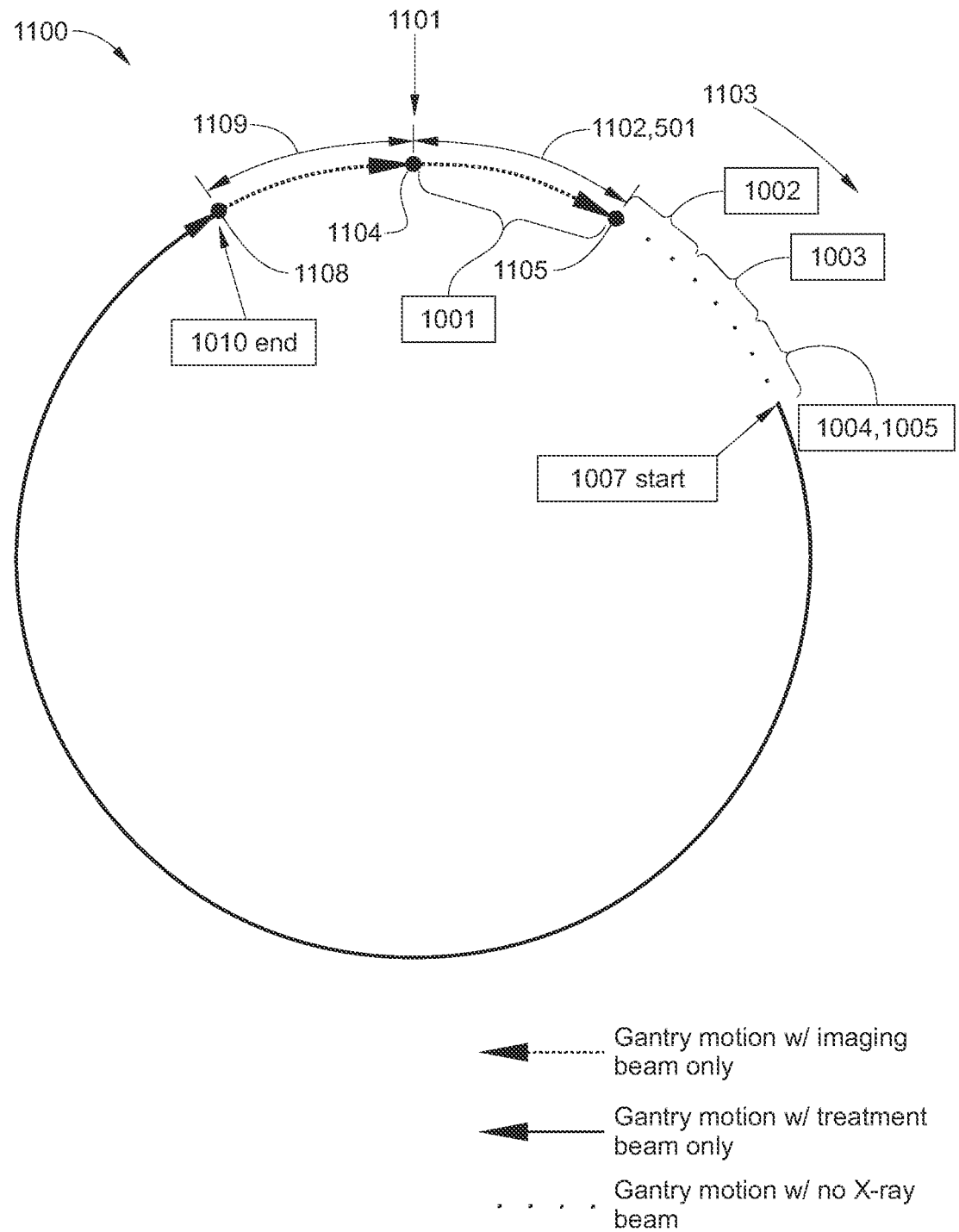
FIGS. 11A and 11B are rotational timelines schematically illustrating at what point in the rotation of a gantry certain method steps occur, according to one or more embodiments of the present disclosure.
Figure 11B:
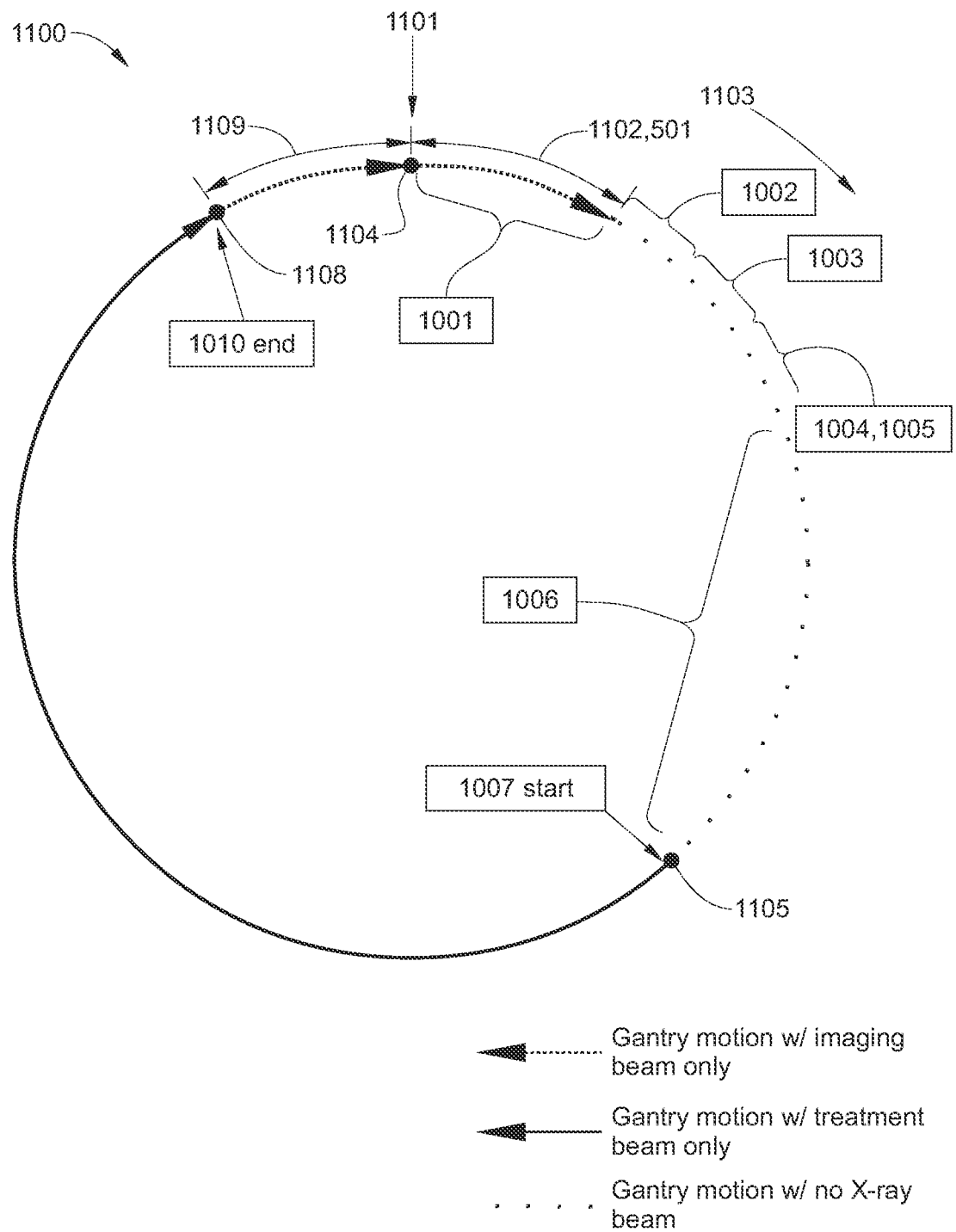
Figure 12:
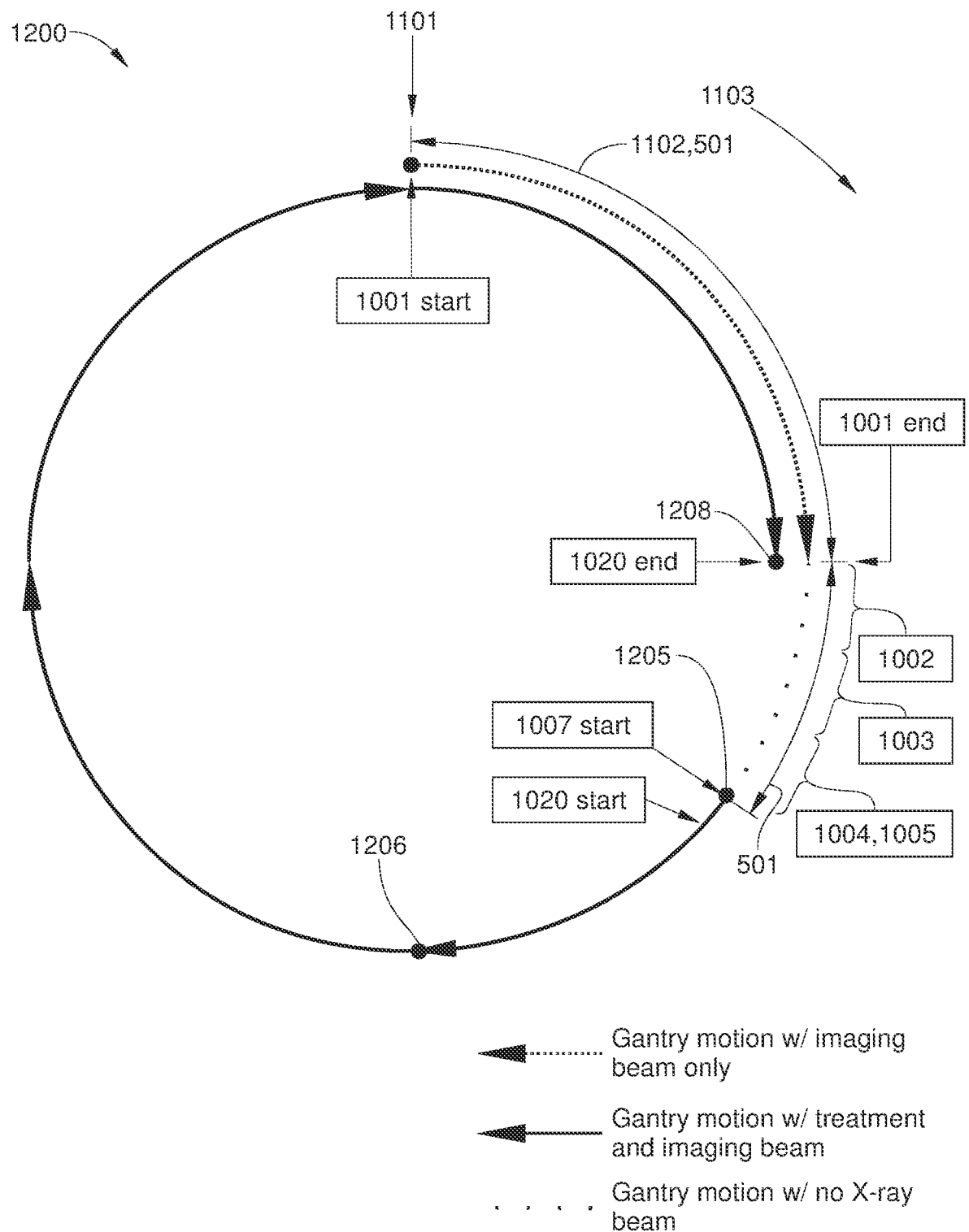
FIG. 12 is a rotational timeline schematically illustrating at what point in the rotation of a gantry certain method steps occur, according to one or more embodiments of the present disclosure.

FIG. 10 sets forth a flowchart of an example computer-implemented method of radiation therapy, according to one or more embodiments of the present disclosure. The method may include one or more operations, functions, or actions as illustrated by one or more of blocks 1001-1040. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-9, persons skilled in the art will understand that any suitably configured radiation therapy system is within the scope of the present disclosure. FIGS. 11A, 11B, and 12 are rotational timelines 1100 and 1200 that each schematically illustrate at what point in the rotation of gantry 210 certain method steps occur, according to one or more embodiments of the present disclosure. Specifically, FIGS. 11A and 11B illustrate at what point in the rotation of gantry 210 certain method steps occur when the process branch that includes steps 1010 and 1011 is implemented, where FIG. 11B illustrates rotation of gantry 210 when the method steps of FIG. 10 are performed in response to a loss of breath hold. FIG. 12 illustrates at what point in the rotation of gantry 210 certain method steps occur when the process branch that includes steps 920 and 921 is implemented. In FIGS. 11A, 11B, and 12, a "12 o'clock" position 1101 corresponds to 0 degrees of rotation by gantry 210.

A method begins at step 1001, when the patient begins a breath hold. In some embodiments, patient breathing is monitored with an optical marker block and camera. In such embodiments, when the operator asks the patient to hold his/her breath, the camera will indicate when the breath is finally held, and step 901 begins. Alternatively, other means of monitoring patient breathing known in the art, such as an optical master block, a waist belt sensor, an optical marker block, breathing tubes, and the like, can be employed in step 901.

In step 1001, a computing device associated with RT system 100 (such as image acquisition and treatment control computer 106) causes the acquisition of volumetric image data from first X-ray imager 207 and second X-ray imager 209 to occur while gantry 210 rotates though an initial imaging arc 1102. For example, while causing gantry 210 to rotate in a first direction 1103 from a first imaging position 1104 to a first treatment delivery position 1105, the computing device causes first imaging X-ray source 206 to direct the imaging X-rays 231 through target volume 410 and second imaging X-ray source 208 to direct imaging X-rays 232 through target volume 410. In some embodiments, pulses of imaging X-rays 231 and imaging X-rays 232 are interleaved to reduce or eliminate noise produced by kV X-ray scatter. In addition, the computing device receives first volumetric image data from first X-ray imager 207 and second volumetric image data from second X-ray imager 209. In some embodiments, the combination of the first volumetric image data and the second volumetric image data corresponds to a complete CBCT data set for target volume 410. Because RT system 100 includes two or more imaging X-ray sources and corresponding X-ray imagers, such a complete CBCT data set can be generated when gantry 210 rotates through an acquisition arc angle 501 of about 90 degrees (i.e., initial imaging arc 1102), as shown in FIG. 12. Alternatively, in some embodiments, DTS images can be generated during initial imaging arc 1102, and initial imaging arc can be a significantly shorter arc, such as about 30 degrees when a target volume is disposed in the abdomen and as small as about 5-10 degrees when a target volume is disposed in the chest. In some embodiments, RT system 100 is configured to rotate gantry 210 through initial imaging arc 1102 at a higher rotational velocity than when treatment beam 230 is being delivered, i.e., through each subsequent acquisition arc angle 501.

In step 1002, the computing device determines the current shape and location of target volume 410, based on the first volumetric image data and the second volumetric image data received in step 1001. It is noted that such a localization of target volume 410 is performed within a 3D set of voxels, rather than a 2D set of voxels, such as a planar array of a single 2D "layer" of voxels employed in MR-based IGRT. Thus, movement and/or deformation of any portion of target volume 410 can be detected by the computing device. That is, such detection of movement or deformation is not contingent on the movement or deformation occurring within a certain planar region of target volume 410 (such as the 2D layer of voxels monitored in MR-based IGRT).

In step 1003, based on the offset determined in step 1002, the computing device determines a locational offset of the current shape and location of target volume 410 from a planned treatment location for target volume 410. For example, in some embodiments, the computing device determines a locational offset of a portion of target volume 410 from a planned treatment location for that portion of target volume 410. Further, in some embodiments, the computing device determines locational offsets for each of a plurality of portions of target volume 410 from respective planned treatment locations for those portions of target volume 410. It is noted that the offset of the current shape and position of target volume 410 from the modified planning target volume can be determined in a 3D digital volume that surrounds target volume 410, rather than in a 2D representation of a planar region that passes through target volume 410.

In step 1004, based on the offset determined in step 1003, the computing device determines whether a portion of target volume 410 is less than a first threshold distance from a planned treatment location for that portion of target volume 410. Further, in some embodiments, the computing device determines whether each of a plurality of portions of target volume 410 is less than the first threshold distance from a respective planned treatment location for the portion of target volume 410. In such embodiments, determining whether a portion target volume 410 is less than the first threshold distance from the planned treatment location for that portion includes determining whether any portion of target volume 410 exceeds an abort treatment threshold, so that an abort of the current treatment is triggered. For example, target volume 410 can move significantly due to peristalsis, bas-bubble motion, loss of patient breath hold, and the like. In some embodiments, the abort treatment threshold can be a total allowable displacement of a portion of target volume 410 from a location designated for that portion in the modified planning target volume. Thus, in such embodiments, when the portion is displaced from the location indicated in the modified planning target volume by more than the abort treatment threshold, the current treatment is aborted, and the method proceeds to step 1040; if the portion is displaced by less than the abort treatment threshold, the method proceeds to step 1005. Alternatively or additionally, in some embodiments, the abort treatment threshold includes an allowable total volume of target volume 410 that extends outside the modified planning target volume. Alternatively or additionally, in some embodiments, the abort treatment threshold includes any other quantifiable metric for displacement of target volume 410 with respect to the modified planning target volume. Thus, step 1004 ensures that if target volume 410 changes position and/or is deformed too much during treatment, the treatment is aborted.

In step 1005, the computing device determines whether the current treatment arc is being performed in response to a loss of breath in a preceding treatment art. If no, the method proceeds to step 1007; if yes, the method proceeds to step 1006.

In step 1006, the computing device causes gantry 210 to rotate to a position that corresponds to a gantry position during a preceding treatment arc at which patient breath hold was lost and treatment beam 230 was turned off. The method then proceeds to step 1007.

In step 1007, while the computing device causes gantry 210 to continue to rotate in first direction 1103 (for example, from a first treatment delivery position 1105 to a second treatment delivery position 1106), the computing device initiates delivery of treatment beam 230 to target volume 410 according to the current treatment plan. In some embodiments, treatment beam 230 is delivered continuously to target volume 410, and in other embodiments treatment beam 230 is not delivered continuously, for example treatment beam 230 can be delivered intermittently and/or via a series of multiple pulses.

In step 1008, while gantry 210 continues to rotate in first direction 1103, the computing device determines whether the current clinical protocol indicates that kV imaging is to be avoided throughout the treatment arc. For example, in some instances, depending on the anatomical site (e.g., lung vs. abdomen) and on the maximum dose rate of LINAC 204, a clinical protocol may indicate that dosing caused by kV imaging should be minimized or otherwise reduced. If the current clinical protocol indicates that kV imaging is to be avoided throughout the treatment arc, the method proceeds to step 1010 (see FIG. 11); if the current clinical protocol does not indicate that kV imaging is to be avoided throughout the treatment arc, the method proceeds to step 1020 (see FIG. 12).

In step 1010, the computing device causes treatment beam 230 to be directed to target volume 410 while gantry 210 rotates from first treatment delivery position 1105 to final treatment delivery position 1108, where final treatment delivery position 1108 is the final location in the rotation arc during which treatment beam 230 is directed to target volume 410 (see FIG. 11). In step 1011, the computing device determines whether gantry 210 has rotated through all treatment positions, i.e., whether gantry 201 has reached final treatment delivery position 1108. If no, the method proceeds to step 1012; if yes, the method proceeds to step 1013. In step 1012, the computing device determines, during application of treatment beam 230 to target volume 410, whether a loss of breath-hold has occurred. If yes, the method proceeds to step 1030; if no, the method returns back to step 1010, and treatment beam 230 continues to be delivered to target volume 410 as gantry 210 continues to rotate toward final treatment delivery position 1108. In some embodiments, loss of breath is determined using the same sensor that initiates the acquisition of volumetric image data from first X-ray imager 207 and second X-ray imager 209 while gantry 210 rotates though initial imaging arc 1102 in step 1001. For example, an optical marker block, spirometer, and the like can be employed to detect loss of breath hold by the patient.

In step 1013, which occurs in response to gantry 210 rotating through all treatment positions and reaching final treatment delivery position 1108, the computing device causes after-arc X-ray images to be generated via first X-ray source 206, second X-ray source 208, first X-ray imager 207, and second X-ray imager 209 as gantry rotates through an after-treatment imaging arc 1109. It is noted that, because multiple X-ray imagers are employed to generate after-arc X-ray images, the length of after-treatment imaging arc 1109 can be significantly less than 180 degrees, or even 90 degrees, and still enable the generation of sufficiently clear projection images to detect intra-fraction motion of target volume 410. For example, when target volume 410 is situated in the abdomen, after-treatment imaging arc 1109 can be on the order of about 30 degrees, whereas when target volume 410 is situated in the chest, after-treatment imaging arc 1109 can be on the order of about 1 to 10 degrees.

In step 1014, the computing device compares the after-arc images generated in step 1013 to pre-treatment X-ray images generated during step 1001. The computing device then computes upper and lower bounds of the dose to organs-at risk (e.g., organs proximate target volume 410) and to the gross tumor volume (i.e., target volume 410) based on motion of target volume 410. The information so computed sets upper and lower bounds of possible hot spots and cold spots that may have occurred during treatment. For example, in some embodiments, a first dose calculation is performed assuming that motion of target volume 410 (indicated by the comparison of after-arc images to pre-treatment X-ray images) occurs when gantry 210 is at first treatment delivery position 1105, and a second dose calculation is performed assuming that motion of target volume 410 indicated by the image comparison occurs when gantry 210 is at final treatment delivery position 1108. Thus, even though motion of target volume 410 is not monitored while gantry 210 rotates through treatment positions, a best case dosing scenario and a worst case dosing scenario are calculated for the motion of target volume 410. The method then proceeds to step 1040, which is the end of the current treatment arc.

In step 1020, which occurs upon determination that the current clinical protocol does not indicate that kV imaging is to be avoided throughout the treatment arc, the computing device causes treatment beam 230 to be directed to target volume 410 according to the planned treatment, while gantry 210 rotates in first direction 1103 from first treatment delivery position 1205 to second treatment delivery position 1206. (see FIG. 12). In addition, the computing device causes first imaging X-ray source 206 to direct the imaging X-rays 231 through target volume 410 and second imaging X-ray source 208 to direct imaging X-rays 232 through target volume 410. In some embodiments, pulses of imaging X-rays 231 and imaging X-rays 232 are interleaved with pulses of treatment beam 230 to reduce or eliminate noise produced by MV X-ray scatter generated by treatment beam 230. In addition, the computing device receives third volumetric image data from first X-ray imager 207 and fourth volumetric image data from second X-ray imager 209. Thus, in step 1020, volumetric image data is acquired over the same rotational arc in which treatment beam 230 is delivered to target volume 410.

In some embodiments, DTS acquisition is performed in step 1020. In such embodiments, when acquired over a specific acquisition arc angle 501, the combination of the third volumetric image data and the fourth volumetric image data corresponds to a DTS data set for target volume 410 that includes sufficient information for localization of target volume 410. The specific acquisition arc angle 501 employed in step 1020 can vary depending on various factors, including tissue types included in target volume 410, size and anatomical location of target volume 410, characteristics of first X-ray imager 207 and second X-ray imager 209, and the like. In addition, in embodiments in which DTS acquisition is performed in step 1020, the specific acquisition arc angle 501 is significantly reduced compared to an acquisition arc angle required for generating a complete CBCT data set. Further, because RT system 100 includes two (or more) imaging X-ray sources and corresponding X-ray imagers, the specific acquisition arc angle 501 needed to acquire sufficient data for localization of target volume 410 is half (or less) than the acquisition arc angle required by an RT system with a single kV imager. For example, in embodiments in which DTS acquisition is employed in step 1020, the specific acquisition arc angle 501 needed to acquire sufficient third volumetric image data and fourth volumetric image data for localization of target volume 410 can be between about 5 degrees and about 45 degrees. In the embodiment illustrated in FIG. 10, the specific acquisition arc angle 501 between first treatment delivery position 1205 and second treatment delivery position 1206 is depicted as about 45 degrees of rotation.

In some embodiments, in addition to acquiring third volumetric image data from first X-ray imager 207 and the fourth volumetric image data from second X-ray imager 209, in step 1020 the computing device also updates the existing volumetric image data for digital volume 400, based on the third volumetric image data and the fourth volumetric image data. Thus, after step 1020, digital volume 400 reflects the current position and shape of target volume 410, as determined based on volumetric image data acquired during rotation of the gantry through an acquisition arc angle 501. In instances in which the existing volumetric image data for digital volume 400 includes CBCT-generated image data acquired as gantry rotates 210 through initial imaging arc 1102, a McKinnon-Bates (MKB) algorithm can be employed in step 1020 to update the existing volumetric image data with DTS-generated image data acquired in step 1020.

In step 1021, the computing device determines whether gantry 210 has rotated through all treatment positions, i.e., to final treatment beam delivery position 1208. Treatment beam 230 is typically planned to be applied throughout a 360-degree arc, for example from first treatment delivery position 1205 to final treatment delivery position 1208. Thus, unless the method is aborted, the computing device causes gantry 210 to rotate through a 360-degree arc while treatment beam 230 is applied to target volume 410. If gantry 210 has rotated through all treatment positions, the method proceeds to step 1023; if not, the method proceeds to step 1022.

In step 1022, the computing device determines, during application of treatment beam 230 to target volume 410, whether a loss of breath-hold has occurred. If yes, the method proceeds to step 1030; if no, the method returns back to step 1020, and treatment beam 230 continues to be delivered to target volume 410 as gantry 210 continues to rotate from second treatment delivery position 1206 toward final treatment delivery position 1208. In step 1023, the computing device updates or generates a record of motions of target volume 410 that have occurred during the current treatment arc. The record can be employed to calculate accumulated dose in target volume 410 and in organs-at-risk. The method then proceeds to step 1040, which is the end of the current treatment arc.

In the method, DTS acquisition of volumetric image data is performed over a specific acquisition arc angle 501, where the acquisition arc angle 501 is selected so that sufficient volumetric image data is generated to enable determination of the current location and/or shape of target volume 410. Thus, the computing device performs localization of target volume 410 (i.e., determines the current location and/or shape of target volume 410) each time that gantry 210 rotates through the specific acquisition arc angle 501. For example, in the embodiment illustrated in FIG. 12, the computing device performs localization of target volume 410 after each 30 degrees of rotation during the 360-degree treatment arc. In other embodiments, the computing device performs localization of target volume 410 more frequently, via DTS reconstructions of digital volume 400 that include a "sliding-arc" or "sliding window" approach. More specifically, the computing device updates existing volumetric image data for digital volume 400 with newly acquired volumetric image data that, by itself, may not include sufficient imaging information to enable localization of target volume 410. One such embodiment is illustrated in FIG. 13.

Figure 13:
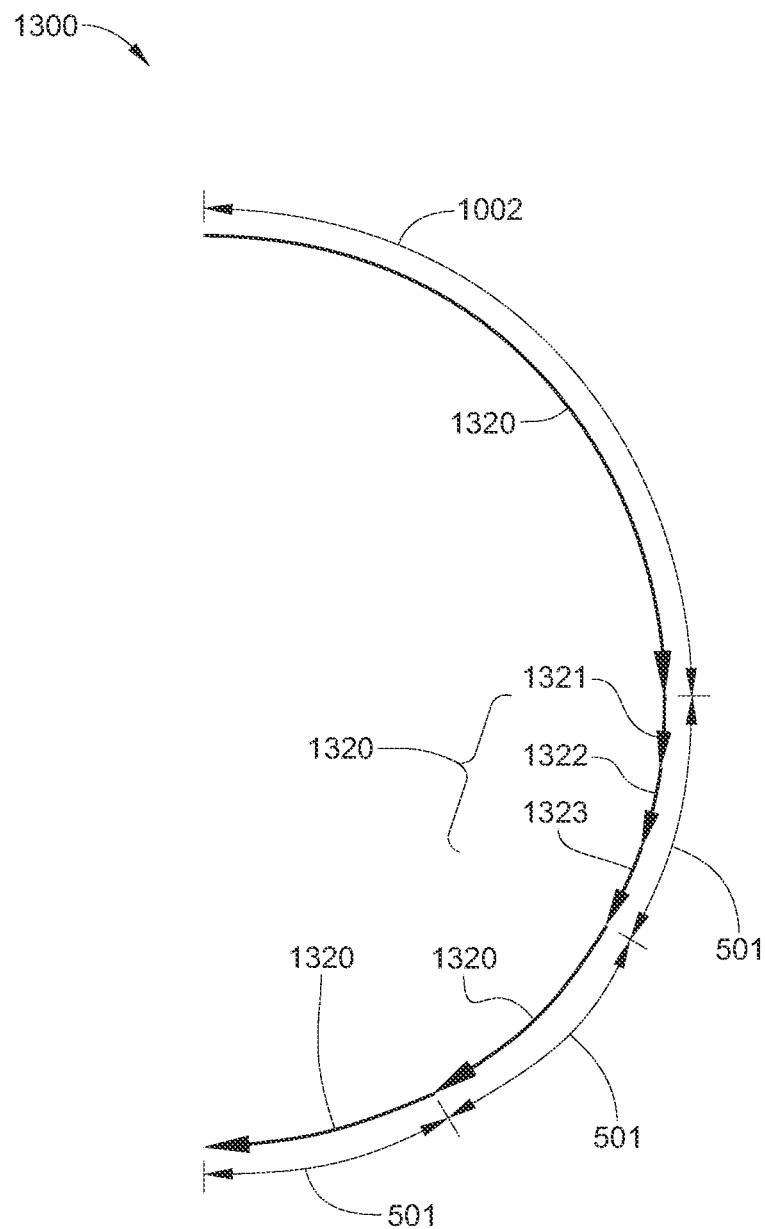
FIG. 13 is a rotational timeline schematically illustrating overlapping image acquisition arcs during the rotation of a gantry, according to one or more embodiments of the present disclosure.

FIG. 13 is a rotational timeline 1300 schematically illustrating overlapping image acquisition arcs during the rotation of gantry 210, according to one or more embodiments of the present disclosure. FIG. 13 shows a portion of the rotation of gantry 210 that includes initial imaging arc 1002 and multiple in-treatment imaging arcs 1321-1323. As noted above, initial imaging arc 1002 occurs prior to application of treatment beam 230 to target volume 410. During initial imaging arc 1002, CBCT acquisition of projection images of target volume 410 takes place for determining the initial location of target volume 410. By contrast, each of in-treatment imaging arcs 1321-1323 corresponds to a different portion of a treatment arc 1320, which is the arc of rotation through which treatment beam 230 is applied to target volume 410. Treatment arc 1320 is typically a 360-degree arc of rotation, but for clarity, only an initial and final portion thereof is shown in FIG. 13.

According to various embodiments, during rotation of gantry 210 through one of in-treatment imaging arcs 1321-1323, a first set of volumetric image data for digital volume 400 is acquired. Existing volumetric image data for digital volume 400 is then updated using the first set of volumetric image data, localization of target volume 410 is performed based on the updated volumetric data for digital volume 400, and modifications to the position of target volume and/or treatment beam 230 are then executed, when appropriate. In this way, feedback regarding the position and deformation of target volume 410 is generated before gantry 210 has rotated through an acquisition arc angle 501 of sufficient magnitude for the generation of a complete set of volumetric image data for target volume 410. Instead, feedback regarding the position and deformation of target volume 410 can be generated at a frequency that is significantly higher than when performing localization of target volume 410 based on a complete set of volumetric image data (generated when gantry 210 rotates through a complete acquisition arc angle 501). For example, in the embodiment illustrated in FIG. 13, acquisition arc angle 501 includes three in-treatment imaging arcs 1321-1323. In such an embodiment, localization feedback can be generated based on updating existing volumetric image data (such as CBCT image data acquired during initial imaging arc 1002) with volumetric image data acquired during a single in-treatment imaging arc (such as in-treatment imaging arc 1321). As a result, localization feedback is received in such an embodiment at three times the frequency of feedback data generated that is based on data acquired during a complete acquisition arc angle 501.

Figure 14:
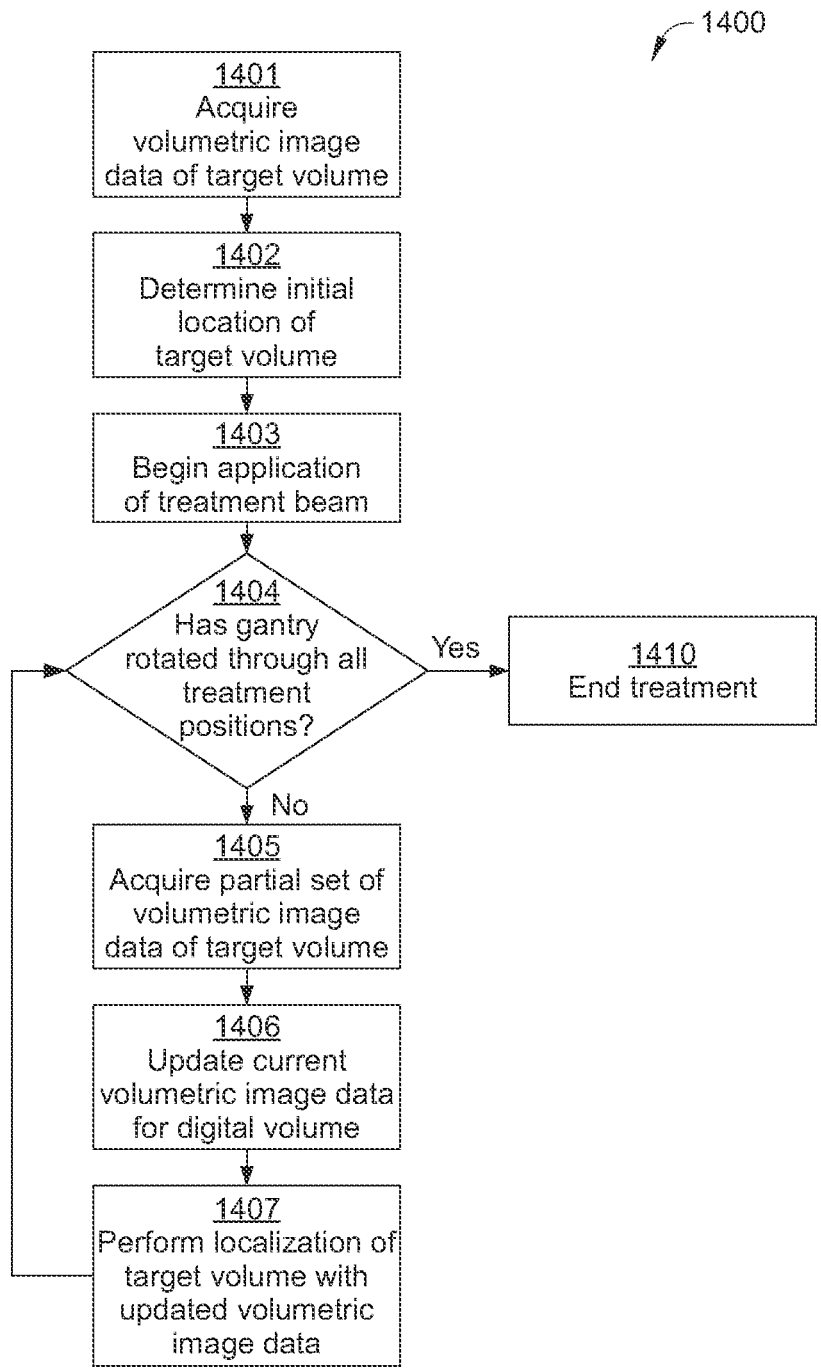
FIG. 14 sets forth a flowchart of an example computer-implemented method of radiation therapy, according to one or more embodiments of the present disclosure.

FIG. 14 sets forth a flowchart of an example computer-implemented method of radiation therapy, according to one or more embodiments of the present disclosure. The method may include one or more operations, functions, or actions as illustrated by one or more of blocks 1401-1410. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-13, persons skilled in the art will understand that any suitably configured radiation therapy system is within the scope of the present disclosure.

A method 1400 begins at step 1401, when the patient begins a breath hold. In step 1401, a computing device associated with RT system 100 (such as image acquisition and treatment control computer 106) causes the acquisition of volumetric image data from first X-ray imager 207 and second X-ray imager 209 to occur while gantry 210 rotates though an initial imaging arc 1002. For example, CBCT acquisition of projection images of target volume 410 takes place during step 1401 to generate a complete set of volumetric image data that enables localization of target volume 410.

In step 1402, the computing device determines the initial location of target volume 410 based on the volumetric image data acquired in step 1401.

In step 1403, the computing device begins application of treatment beam 230 to target volume 410.

In step 1404, the computing device determines whether gantry 210 has rotated through all treatment positions, for example 360 degrees of rotation with treatment beam 230 on. If yes, method 1400 proceeds to step 1410 and treatment ends; if no, method 1400 proceeds to step 1405.

In step 1405, as gantry 210 continues to rotate through the current in-treatment imaging arc (i.e., one of in-treatment imaging arcs 1321-1323), the computing device causes DTS acquisition of projection images of target volume 410 to take place. That is, the computing device causes a partial set of DTS volumetric image data to be acquired for digital volume 400.

In step 1406, the computing device generates updated volumetric image data by updating the current volumetric image data for digital volume 400 with the partial set of DTS volumetric image data acquired in step 1405. In the first iteration of step 1406, the current volumetric image data for digital volume 400 corresponds to the complete set of volumetric image data acquired in step 1401. In subsequent iterations of step 1406, the current volumetric image data for digital volume 400 corresponds to volumetric image data that has been previously updated with DTS volumetric image data, acquired as gantry 210 rotated through earlier in-treatment imaging arcs.

In step 1410, the computing device ends the current treatment and the patient can release the breath hold.

Implementation of the above-described embodiments enables near real-time feedback of anatomical variations during radiation therapy using X-ray imaging techniques. For example, X-ray imaging data for 3D localization of a target volume can be refreshed on the order of about one time or more per second. Thus, during a single breath hold, which can last for 10, 20, 30 seconds or more, the location and deformation of a target volume can be determined repeatedly during the application of a treatment beam. As a result, X-ray imaging can be employed during IGRT for accurate localization of the target volume, and dose calculations can be performed that quantify the possible positional bounds of hot spots and cold spots that develop during treatment.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A radiation treatment system comprising:
   a gantry that is rotatably coupled to a drive stand and is configured to rotate about a bore of the radiation treatment system;
   a treatment-delivering X-ray source mounted on the gantry and configured to direct treatment X-rays to a target volume of a patient disposed in the bore;
   an imaging X-ray source mounted on the gantry;
   an X-ray imager mounted on the gantry; and
   a processor configured to:
   cause the gantry to rotate continuously in a first direction from a first treatment delivery position to a second treatment delivery position;
   while causing the gantry to rotate in the first direction from the first treatment delivery position to the second treatment delivery position, cause the imaging X-ray source to direct X-rays through the target volume and toward the X-ray imager;
   receive a first set of X-ray projection images from the X-ray imager in response to the X-rays being directed toward the X-ray imager;
   based on the first set of X-ray projection images, monitor the patient for a loss of breath hold; and
   in response to a determination that the patient has not lost breath hold:
   cause the gantry to continue to rotate to the second treatment delivery position; and
   while causing the gantry to continue to rotate to the second treatment delivery position, initiate delivery of a treatment beam of the treatment-delivering X-ray source to the target volume.

2. The radiation treatment system of claim 1, wherein the processor is further configured to, while causing the gantry to continuously rotate in the first direction from a first imaging position to a second imaging:
   cause the imaging X-ray source to direct initial X-rays through the target volume;
   receive an initial set of X-ray projection images from the X-ray imager, wherein the initial set of X-ray projection images are based on the initial imaging X-rays; and
   determine an initial location of the target volume based on the initial set of X-ray projection images.

3. The radiation treatment system of claim 2, wherein the initial set of X-ray projection images are generated via a cone-beam computed tomography process.

4. The radiation treatment system of claim 2, wherein, when the processor causes the gantry to rotate continuously in the first direction from the first treatment delivery position to the second treatment delivery position, the processor to causes the gantry to rotate continuously in the first direction through the first imaging position, the second imaging position, the first treatment delivery position, and the second treatment delivery position in a single rotation.

5. The radiation treatment system of claim 2, wherein when rotating in the first direction, the gantry passes through the second imaging position prior to passing through the first treatment delivery position.

6. The radiation treatment system of claim 2, wherein the processor is further configured to:
   based on the initial location of the target volume, determine that the initial location of the target volume is less than a threshold distance from the planned treatment location; and initiate delivery of the treatment beam of the treatment-delivering X-ray source to the target volume based in part of the determination that the initial location of the target volume is less than the threshold distance from the planned treatment location.

7. The radiation treatment system of claim 1, wherein the processor is configured to monitor the patient for the loss of breath hold by determining a current location of the target volume based on the first set of X-ray projection images.

8. The radiation treatment system of claim 7, wherein determining the current location of the target volume based on the set of X-ray projection images comprises:
based on an initial set of X-ray projection images, generating image data for a digital volume that includes the target volume, wherein the initial set of X-ray projection images are received while the processor causes the gantry to rotate continuously in the first direction from a first imaging position to a second imaging position;
updating the image data for the digital volume based on the first set of X-ray projection images; and
after updating the image data for the digital volume, determining the current location of the target volume based on the image data for the digital volume.

9. The radiation treatment system of claim 1, wherein the imaging X-ray source and the X-ray imager are operable to be positioned on the gantry in a half-fan configuration.

10. The radiation treatment system of claim 1, wherein the imaging X-ray source and the X-ray imager are operable to be positioned on the gantry in a full-fan configuration.

11. The radiation treatment system of claim 10, wherein the imaging X-ray source and the X-ray imager are configured to be adjustable from the full-fan configuration to a half-fan configuration.

12. The radiation treatment system of claim 10, wherein the X-ray imager is movably mounted on the gantry and is operable to be moved from a full-fan position to a half-fan position.

13. The radiation treatment system of claim 10, wherein the imaging X-ray source is movably mounted on the gantry and is operable to be moved from a full-fan position to a half-fan position.

14. The radiation treatment system of claim 10, wherein the second imaging X-ray source includes a collimator configured to change between a half-fan position and a full-fan position.

15. A radiation treatment system comprising:
a gantry that is rotatably coupled to a drive stand and is configured to rotate about a bore of the radiation treatment system;
a treatment-delivering X-ray source mounted on the gantry and configured to direct treatment X-rays to a target volume of a patient disposed in the bore;
an imaging X-ray source mounted on the gantry;
an X-ray imager mounted on the gantry; and
a processor configured to:
cause the gantry to rotate continuously in a first direction through a first treatment arc that includes a first treatment delivery position and a second treatment delivery position;
while causing the gantry to rotate through the first treatment arc in the first direction from the first treatment delivery position to the second treatment delivery position, cause the imaging X-ray source to direct X-rays through the target volume and toward the X-ray imager;
receive a set of X-ray projection images from the X-ray imager in response to the X-rays being directed toward the X-ray imager;
based on the set of X-ray projection images, monitor the patient for a loss of breath hold; and
in response to a determination that the patient has lost breath hold:
store a gantry angle at which the patient has lost breath hold; and
end the first treatment arc.

16. The radiation treatment system of claim 15, wherein the processor is further configured to, in response to determining that the patient has lost breath hold, prevent delivery of the treatment beam to the target volume while causing the gantry to continue to rotate to the second treatment delivery position.

17. The radiation treatment system of claim 15, wherein the processor is further configured to, in response to determining that the patient has lost breath hold, perform a second treatment arc that begins at the gantry angle and completes the first treatment arc.

18. The radiation treatment system of claim 17, wherein the processor is further configured to perform the second treatment arc by:
causing the gantry to rotate in the first direction to the gantry angle; and
while causing the gantry to rotate in the first direction to the gantry angle, preventing delivery of the treatment beam.

19. The radiation treatment system of claim 18, wherein the processor is further configured to perform the second treatment arc by:
determining that the current location of the target volume is less than a threshold distance from a planned treatment location; and
in response, while causing the gantry to rotate in the first direction from the gantry angle, initiating delivery of the treatment beam to the target volume while causing the gantry to continue to rotate in the first direction.

20. The radiation treatment system of claim 15, wherein the processor is further configured to end the first treatment arc by preventing delivery of the treatment mean to the target volume while causing the gantry to continue to rotate in the first direction from the gantry angle.

* * * * *